(12) United States Patent
Kanno et al.

(10) Patent No.: US 6,183,250 B1
(45) Date of Patent: Feb. 6, 2001

(54) LOCK FOR ORTHODONTIC TREATMENT

(75) Inventors: Yoneo Kanno, Nagareyama; Yusei Kadobayashi, Kyoto, both of (JP)

(73) Assignee: Shofu, Inc., Kyoto (JP)

( * ) Notice: Under 35 U.S.C. 154(b), the term of this patent shall be extended for 0 days.

(21) Appl. No.: 09/322,019

(22) Filed: May 28, 1999

Related U.S. Application Data

(63) Continuation of application No. 08/894,716, filed as application No. PCT/JP96/03834 on Dec. 26, 1996, now abandoned.

(30) Foreign Application Priority Data

Dec. 27, 1995 (JP) .................................................. 7-351150

(51) Int. Cl.⁷ .................................................. A61C 3/00
(52) U.S. Cl. .............................................. 433/17; 433/18
(58) Field of Search ................................. 433/8–17, 18, 433/22

(56) References Cited

U.S. PATENT DOCUMENTS

| | | | |
|---|---|---|---|
| 1,280,628 | * 10/1918 | Angle | 433/14 |
| 1,429,749 | 9/1922 | Maeulen et al. | |
| 3,218,714 | * 11/1965 | Wallshein | 433/17 |
| 4,091,540 | * 5/1978 | Wellshein | 433/21 |
| 4,350,487 | 9/1982 | Kesling et al. | |
| 4,354,834 | * 10/1982 | Wilson | 433/21 |
| 4,392,826 | * 7/1983 | Goshgarian | 433/7 |
| 4,764,112 | 8/1988 | Bergersen | |
| 4,897,035 | * 1/1990 | Green | 433/17 |
| 5,707,232 | * 1/1998 | Strauss et al. | 433/17 |

FOREIGN PATENT DOCUMENTS

| | | | |
|---|---|---|---|
| 667 040 | * 11/1938 | (DE) | 433/17 |
| 56-167910 | 12/1981 | (JP) . | |
| 418572 | 4/1992 | (JP) . | |
| 434901 | 6/1992 | (JP) . | |
| 448177 | 11/1992 | (JP) . | |

OTHER PUBLICATIONS

European Search Report dated Jul. 26, 2000.

\* cited by examiner

*Primary Examiner*—Nicholas D. Lucchesi
(74) *Attorney, Agent, or Firm*—Stevens, Davis, Miller & Mosher, L.L.P.

(57) ABSTRACT

A lock for orthodontic treatment comprises a holding member fixed to a molar band, and a spring wire having an end removably held by the holding member. The holding member is configured such that the end of the spring wire is held on the holding member by being moved axially along the holding member. One of the holding member and the spring wire has elasticity in a direction perpendicular to its axis. The holding member includes a first engagement portion for preventing the movement of the end of the spring wire in a mounting direction, and a second engagement portion for preventing the movement of the end of the spring wire in a removing direction. The spring wire includes a first locking portion for engaging with the first engagement portion of the holding member, and a second locking portion for engaging with the second engagement portion of the holding member.

34 Claims, 28 Drawing Sheets

LOCK FOR ORTHODONTIC TREATMENT

CROSS REFERENCE TO RELATED APPLICATIONS

This is an continuation application of U.S. Ser. No. 08/894,716, filed Aug. 26, 1997, now abandoned; which, in turn, is a 371 of PCT/JP96/03834, filed Dec. 26, 1996.

TECHNICAL FIELD

The present invention relates to a lock for orthodontic treatment.

BACKGROUND ART

As a lock for orthodontic treatment, a lock called "ST lock" has been generally known so far. As shown in FIG. 56, this lock has a locking portion formed at an end of a wire "a" (shown as formed at opposite ends of the wire in the drawing). The locking portion includes a bent-down portion "b" formed proximally to a distal end of the wire "a", a horizontal portion "c" extending distally from the bentdown portion "b", a bent-up portion "d" formed at a distal end of the horizontal portion "c", and a short pin "e" and a long pin "f" brazed at position "g" between the bent-down portion "b" and the bent-up portion "d". As shown with respect to one of the locking portions, the short pin "e" and the bent-up portion "d" are inserted respectively into a pipe P1 and a pipe P2 which are fixedly attached to a band B fitted on a molar tooth. The long pin "f" is bent onto and fixed to the top end of the pipe P1. The "ST" lock is comparatively easy to mount in position, but on the other hand the process of fixing the short and long pins to the wire "a" by brazing involves a very troublesome operation in fabricating the device, because the wire "a" is a material having a thickness of less than 1 mm. Another problem with the device is that comparatively fragile brazed portions are liable to become damaged when a strong pull is applied upon the device in use.

As another type of lock, a lock called "lingual lock" is described in Japanese Utility Model Publication No. 4-18572. This device includes lock portions formed adjacent to a distal end of a wire by bending the wire in a hairpin-like fashion at two locations spaced a specified distance. The lock portions are press-fitted respectively into two tubes fixedly provided on a molar tooth band with a specified distance. With this lock, the problem is that high technical skill and precise care are required in the fabrication of the device because the hairpin-like bent portions must be spaced precisely as designed. Another problem is that since the hairpin-like bent portions are inserted into the tubes and held in position merely by frictional force, there is a danger of their slipping off the tube.

DISCLOSURE OF THE INVENTION

In view of these problems with the prior art, the present invention has an object to provide a lock for orthodontic treatment which is comparatively easy to fabricate, simple to handle for locking, has no fragile part liable to damage during use, and can ensure enhanced safety.

In order to accomplish the object, a lock for orthodontic treatment in accordance with the present invention comprises a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member.

In one embodiment of the invention, the holding member is preferably a holding tube of cylindrical shape into which the spring wire is to be inserted.

In this case, one of the holding tube and the spring wire may have elasticity in a direction perpendicular to the axis thereof. In order to enable the spring wire to have such elasticity, a distal end of the spring wire may be bent to form a spring hook portion. In order to enable the holding tube to have elasticity, the holding tube may be formed with a slit in a longitudinal direction thereof.

In another embodiment of the invention, the holding member preferably has a sectional configuration of H shape or channel shape which comprises a web portion and flange portions extending from both ends of the web portion.

In this case, in order to enable the spring wire to have elasticity, a distal end of the spring wire may be bent to form a spring hook portion.

The lock for orthodontic treatment of the invention constructed as described above is easy to fabricate because it involves no such particular difficulty or complicated job, or high skill as have been required in the manufacture of prior art devices. In use, the spring wire is simply moved axially. To disengage the lock, it is only necessary to push down or push up the outer end of the spring wire, then pull out the wire. Therefore, the device is far much more simple to handle than conventional devices. Locking is positively performed through engagement between the cutout surface portion and the engagement surface portion. In addition, the device has no such fragile part as has been found with prior art devices. Thus, safety in use can be further enhanced.

BEST MODE FOR CARRYING OUT THE INVENTION

Embodiment 1

Figure 1:
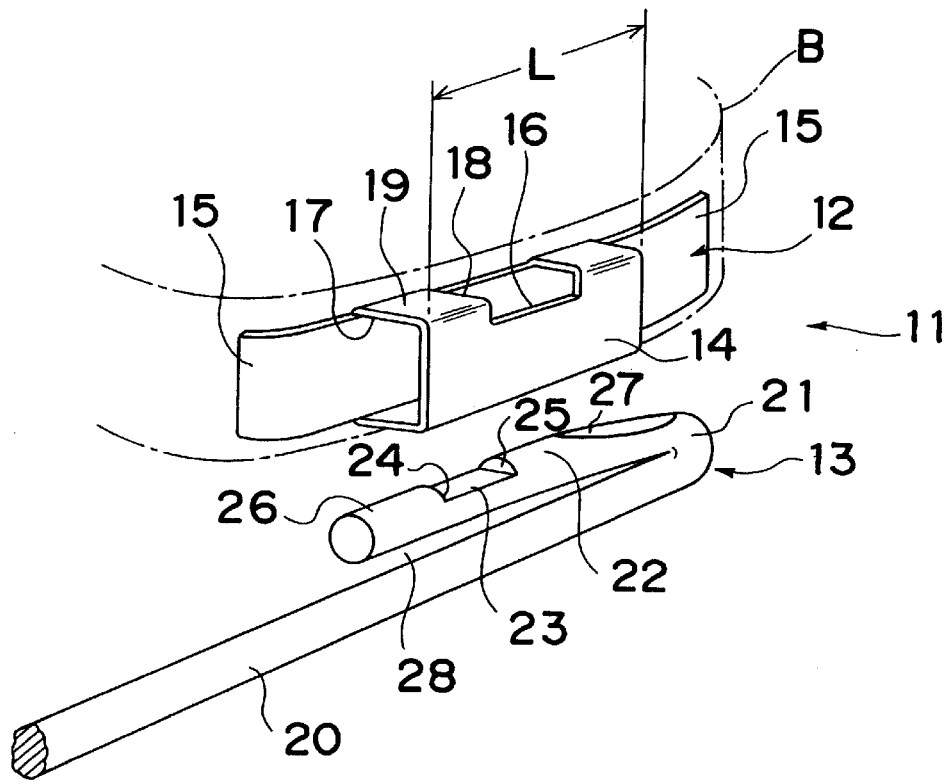
FIG. 1 is a perspective view of an embodiment 1 of the lock for orthodontic treatment of the invention in disengaged condition.
Figure 2:
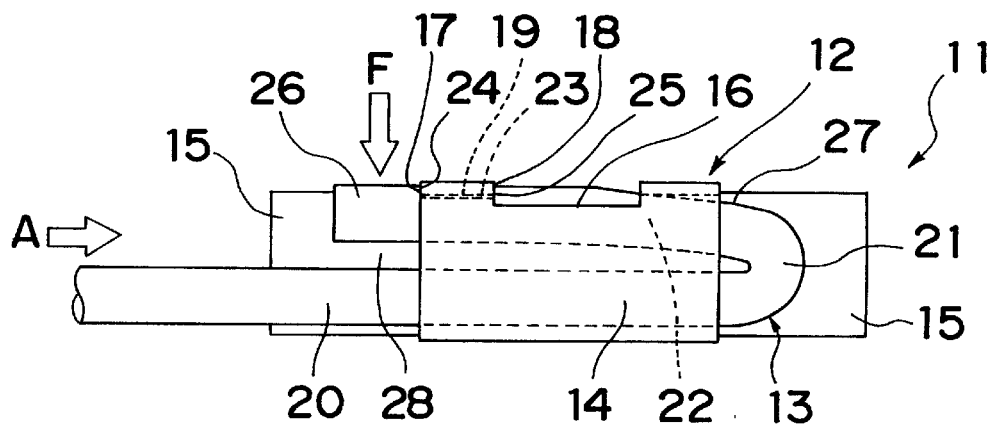
FIG. 2 is a front view of the lock shown in FIG. 1 in engaged condition.

FIGS. 1 and 2 illustrate a lock representing a first embodiment of the present invention. Reference numeral 11 designates the lock as a whole; 12 designates a holding tube of the device, and 13 designates a spring wire.

The holding tube 12 includes a tubular portion 14 fixed to a molar tooth band B. The tubular portion 14 is transversely disposed along the length (in the circumferential direction) of the band B. One side of the tubular portion extends laterally to form wing portions 15 so as to be readily affixed to the band B by spot welding or brazing. On the top side of tubular portion 14 there is provided a window 16 along with an engagement surface portion 19 having a pair of engaging edges 17, 18. The length L of the tubular portion 14 is generally 3 to 5 mm, preferably 3 to 4 mm.

The spring wire 13 includes a linearly extending wire body 20 and a spring hook portion 22 formed by bending the wire at a position adjacent the end of the wire body, that is, at a curved portion 21. A required space 28 is provided between the spring hook portion 22 and the wire body 20. The distance between respective outer sides of the wire body 20 and the spring hook portion 22 is defined slightly larger than the inner diameter of the tubular portion 14.

Figure 18:
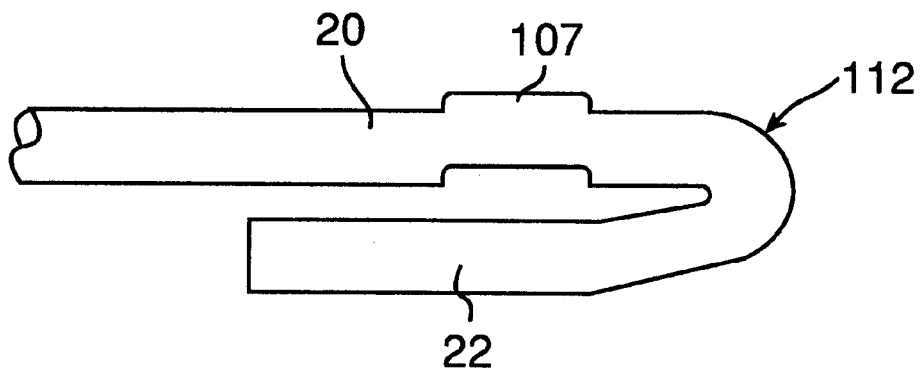
FIG. 18 is an explanatory view of a prior art device.

In the figures, the wire body 20 is shown with respect to its one end side only. However, in the same way as wire "a" shown in FIG. 18, the wire body 20 may be bent in an arch-shaped fashion and formed with spring hook portions 22 at both ends. Preferably, the spring wire 13 is made of stainless steel, for example.

On the upper side of the spring hook portion 22 there is provided a shallow cutout surface portion 23 for receiving the engagement surface portion 19 of the tubular portion 14. The cutout surface portion 23 is formed with end edges 24, 25 at opposite ends thereof. An outer end portion 26 of the spring hook portion 22 is extended so that it projects from an engaging edge 17 when the spring hook portion 22 is fitted into the tubular portion 14.

To fit the spring wire 13 into the holding tube 12, the spring wire 13 is inserted into the tubular portion 14 in the direction of arrow A as shown in FIG. 2 with the curved portion 21 positioned on the fore side. Thereby, the spring hook portion 22 is pressed by the engagement surface portion 19 so that the space 28 between the spring hook portion 22 and the wire body 20 is shortened. When the wire body 20 is further forced in, the cutout surface portion 23 coincides with the engagement surface portion 19 of the tubular portion. Then, the spring hook portion 22 expands outward by its own elasticity so that ends 24, 25 of the cutout surface portion 23 come into engagement with the engaging edges 17, 18 of the engagement surface portion 19, whereby automatic locking is effected. In this locked state, the wire body 20, even when pushed or pulled, is prevented from slipping off the holding tube 12.

In order to disengage the lock to remove the wire body 20, the outer end portion 26 is pressed against the elastic force in the direction of arrow F as shown in FIG. 2. Thereby, the spring hook portion 22 is flexed to allow the cutout surface portion 23 to move away from the engagement surface portion 19, which caused the engagement relationship between the end edges 24, 25 of the cutout surface portion 23 and the engaging edges 17, 18 of the engagement surface portion 19 to be released. The spring wire 13 can be easily pulled out of the holding tube 12 by pulling the wire body 20 or by pushing the curved portion 21 in a direction opposite to the direction of arrow A.

The reference numeral 27 designates a flank provided as required between the cutout surface portion 23 of the spring hook portion 22 and the curved portion 21. The provision of the flank 27 permits easy insertion of the spring hook portion 22 into the tubular portion 14 and easy removal of the same.

In this embodiment, only one side of the window 16 of the holding tube 12 is used as the engagement surface portion 19. However, both sides of the window 16 may be used as a pair of engagement surface portions 19. In this case, one of the pair of engagement surface portions 19 may be selected for engagement with the cutout surface portion 23 of the spring hook portion 22, whereby the spring wire 13 can be adjusted in length. Also, the spring hook portion 22 may be formed with a pair of cutout surface portions 23 in complementary relation to the pair of engagement surface portions 19 of the holding tube 12.

Figure 1A:
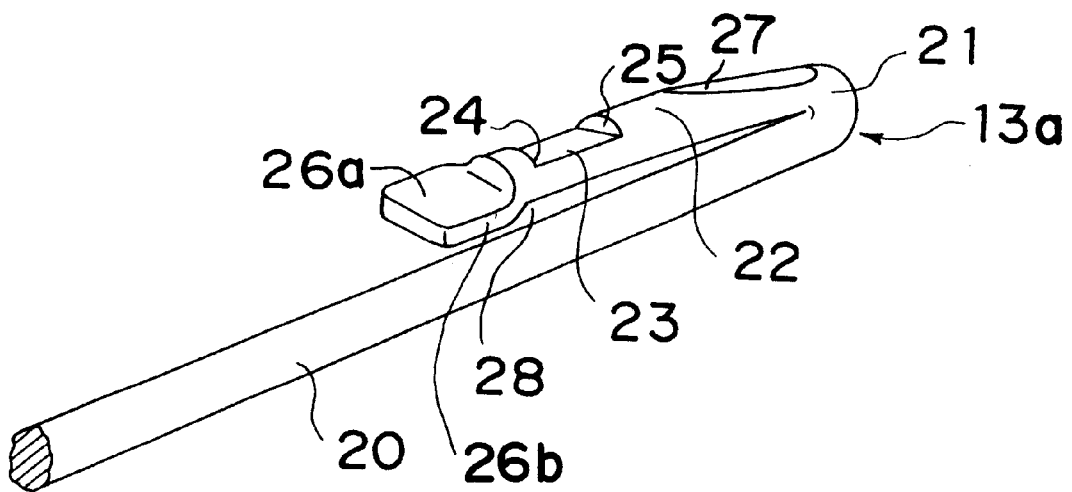
FIG. 1A is a perspective view of a modified form of the spring wire of the lock shown in FIG. 1.

A spring wire 13a shown in FIG. 1A is one such that the outer end portion 26 of the spring wire 13 shown in FIG. 1 is formed with a flat crushed portion 26a. When the spring wire 13a is inserted into the holding tube 12, a shoulder portion 26b of the flat crushed portion 26a engages with a vertical edge formed in continuation to the engaging edge 17 of the holding tube 12, preventing the spring hook portion 22 from projecting through the holding tube 12. Such a crushed portion 26a is equally applicable to the spring wire in any of embodiments and modifications to be described hereinafter.

Embodiment 2

With respect to the following embodiments, only different parts will be described, and substantially identical parts will be designated by the same reference numerals so that description of such parts is omitted.

Figure 3:
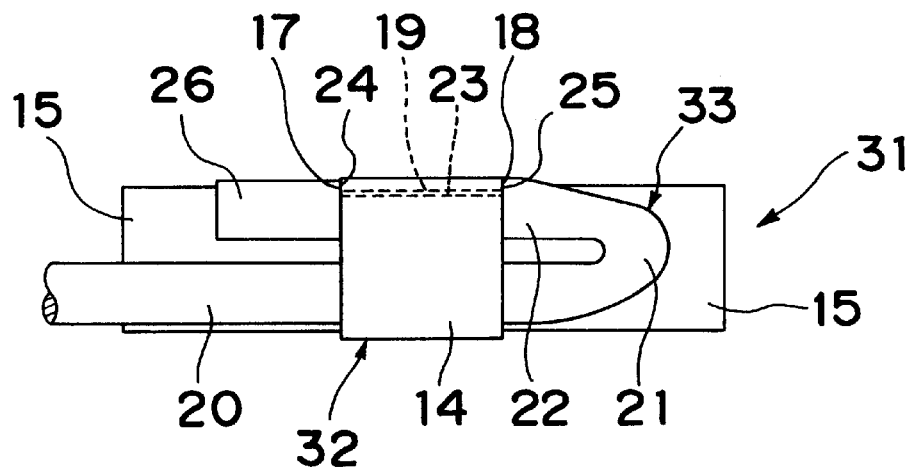
FIG. 3 is a front view of an embodiment 2 of the lock of the invention in engaged condition.

FIG. 3 shows a lock 31 representing a second embodiment of the invention. The tubular portion 14 of a holding tube 32 of the present embodiment is different from that of the first embodiment in that it has no such window 16 as shown in FIGS. 1 and 2. On both ends of the upper side of the tubular portion 14, there are formed engaging edges 17, 18 so that the upper side in its entirety defines an engagement surface portion 19. A shallow cutout surface portion 23 is formed generally centrally of a spring hook portion 22 of a spring wire 33 so that end edges 24, 25 mechanically engage with the engaging edges 17, 18.

The embodiment illustrated in FIG. 3 is especially suitable for application in the case where available space is not sufficient to accommodate the same length of tubular portion 14 as in the embodiment shown in FIGS. 1 and 2, for example where the lock is to be mounted to a tooth other than molar tooth. This embodiment provides accurate locking through mechanical engagement between the engaging edge 17, 18 of the engagement surface portion 19 and end edge 24, 25 of the cutout surface portion 23, and ease of insertion/removal handling, and in these respects it is equal to the embodiment shown in FIGS. 1 and 2.

Embodiment 3

Figure 4:
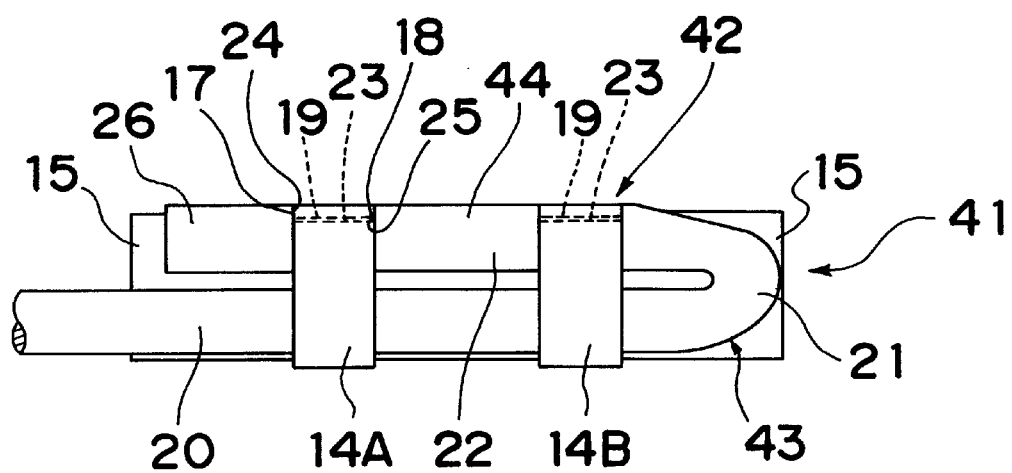
FIG. 4 is a front view of an embodiment 3 of the lock of the invention in engaged condition.

FIG. 4 illustrates a lock 41 representing a third embodiment of the invention. In this lock 41, a holding tube 42 is formed with two tubular portions 14A, 14B arranged on the wing portion 15 with a required space portion 44 therebetween. The upper side of each tubular portion 14A, 14B functions as an engagement surface portion 19, with engaging edges 17, 18 formed at opposite sides. A spring hook portion 22 of a spring wire 43 is also formed with two cutout surface portions 23 in complementary relation to the tubular portions 14A, 14B. Each cutout surface portion 23 is provided at both ends thereof with end edges 24, 25 adapted to engage with the engaging edges 17, 18. An outer end portion of the spring hook portion 22 is made to project from the tubular portion 14A.

This third embodiment provides more powerful locking effect than the foregoing two embodiments in that mechanical locking is performed by means of two tubular portions 14A, 14B and two cutout surface portions 23. For the purpose of disengaging the lock, it is preferable that the outer end portion 26 be pushed down as in the case of FIG. 2 and, at the same time, a portion intermediate between the two tubular portions 14A, 14B be depressed. However, such simultaneous depression of the intermediate portion is not always required if adjustment is made with respect to the distance between the wire body 20 and the spring hook portion 22, and the thickness of the engagement surface portion 19, Embodiment 4

Figure 5:
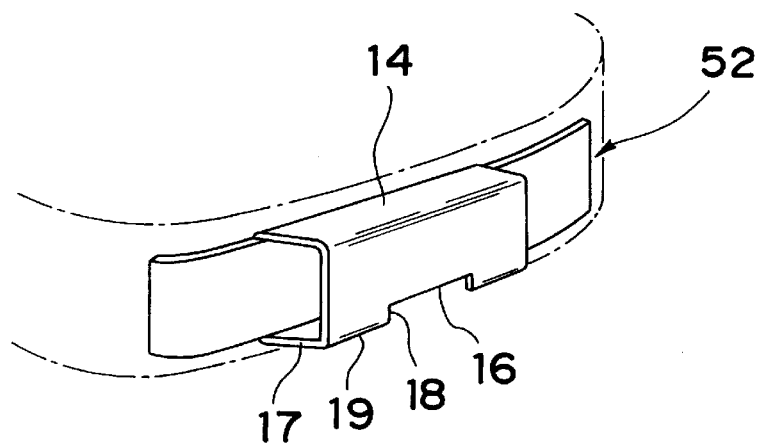
FIG. 5 is a perspective view of a holding tube in an embodiment 4 of the lock of the invention.

FIG. 5 illustrates a holding tube 52 of a lock representing a fourth embodiment of the invention. This embodiment differs from the first embodiment in that a window 16 is provided on the underside of the tubular portion 14. Where the window 16 is located on the underside, the spring hook portion 22 is positioned at the lower side and the wire body 20 is positioned at the upper side. This provides a feature that the device can be used with a gap provided between the wire body 20 and the gum as required. Other construction feature and effect are same as those of the first embodiment.

Embodiment 5

Figure 6:
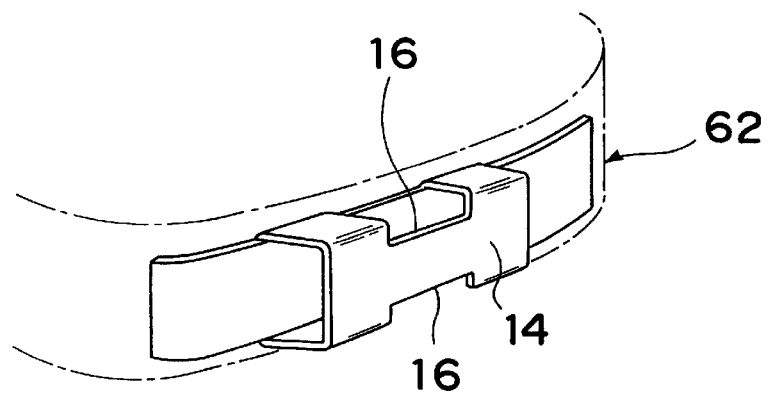
FIG. 6 is a perspective view of a holding tube in an embodiment 5 of the lock of the invention.

FIG. 6 shows a holding tube 62 of a lock representing a fifth embodiment of the invention. This embodiment differs from the third and fourth embodiments in that two windows 16 are provided at upper and lower sides of the tubular portion 14. The provision of the windows 16 on both upper and lower sides offers convenience such that in use, the spring hook portion 22 may be positioned on upper side or, where necessary, may be positioned on lower side. Other construction feature and effect are same as those in the case of the first and fourth embodiments.

Embodiment 6

Figure 7:
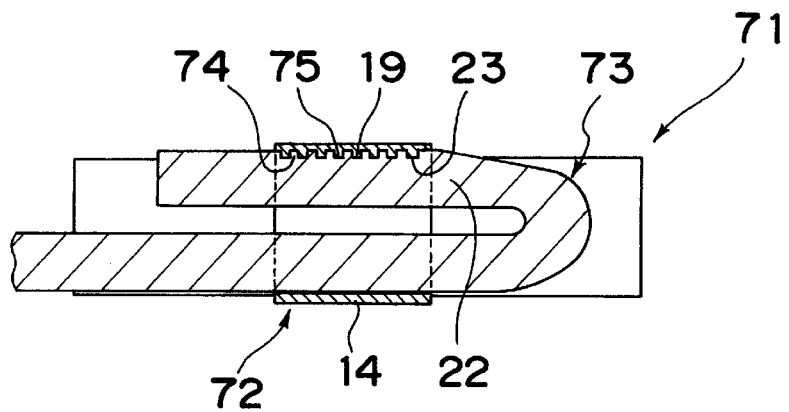
FIG. 7 is a sectional view of an embodiment 6 of the lock of the invention in engaged condition.

FIG. 7 shows a lock 71 representing a sixth embodiment of the invention. In this embodiment, an engagement surface portion 19 similar to the second embodiment in FIG. 3 is formed thereon with projections and depressions 74 in succession. Also, a cutout surface portion 23 is formed thereon with complementary depressions and projections 75 for lock engagement with the projections and depressions 74. The spring hook portion 22, when inserted into the tubular portion 14, is securely fixed in position by means of the engagement surface portion 19 and the cutout surface portion 23. Other construction feature and effect are same as those in the case of the second embodiment.

Figure 8:
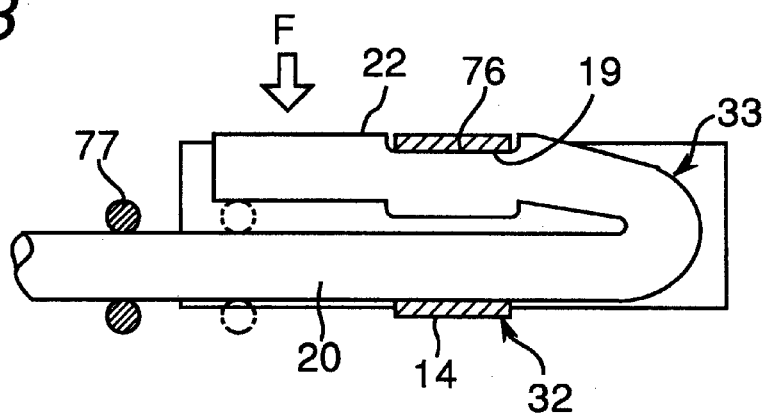
FIG. 8 is a front view of a modified form of the spring wire of the lock shown in FIG. 3.

FIG. 8 shows a spring wire 33 having an engagement recess portion 76 formed thereon by bending or pressing the spring hook portion 22. The engagement recess portion 76 takes the place of the cutout surface portion 23 in the second embodiment. The engagement recess portion 76 is easier to form and more excellent in strength than the cutout surface portion 23.

In order to strengthen the locking function of the spring wire 33, the wire body 20 may be fitted with a ring 77 preferably made of rubber (rubber band) as shown in FIG. 8. The ring 77 should be kept away from the spring hook portion 22 before the spring wire 33 is inserted into the tubular portion 14. After insertion of the spring wire, the ring 77 is set between the spring hook portion 22 and the wire body 20 as shown by a phantom line. This arrangement prevents deformation of the spring hook portion 22 due to a force acting thereon in the direction of arrow F. Therefore, the engagement between the engagement surface portion 19 of the tubular portion 14 and the engagement recess portion 76 of the spring wire 33 is maintained, there being no possibility of the spring wire 33 becoming disengaged from the tubular portion 14. This ring 77 is also applicable to various other embodiments and modifications to be described hereinafter with respect to locks comprising a spring wire having a spring hook portion, and a holding tube.

Figure 9:
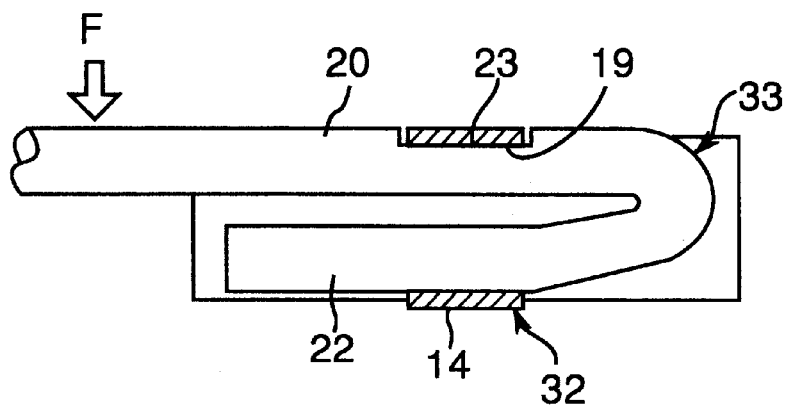
FIG. 9 is a front view of an another modified form of the spring wire of the lock shown in FIG. 3.

FIG. 9 shows a spring wire 33 having a cutout surface portion 23 formed on the wire body 20 instead of the cutout surface portion 23 formed on the spring hook portion 22 of the spring wire 33 as shown in FIG. 3. The locking function of the cutout surface portion 23 of the wire body 20 is similar to that of the cutout surface portion 23 of the spring hook portion 22 in the above described embodiment. In order to remove the spring wire 33 shown in FIG. 9, it is necessary to depress the wire body 20, not the spring hook portion 22, in the direction of arrow F. This, as compared with the case in which the cutout surface portion 23 is formed on the spring hook portion 22, provides an advantage that the depressing position is not limited and smaller pressing force is required. The spring wire 33 may be advantageously used when it is desirable to provide a gap between the wire body 20 and the gum.

Embodiment 7

Figure 10:
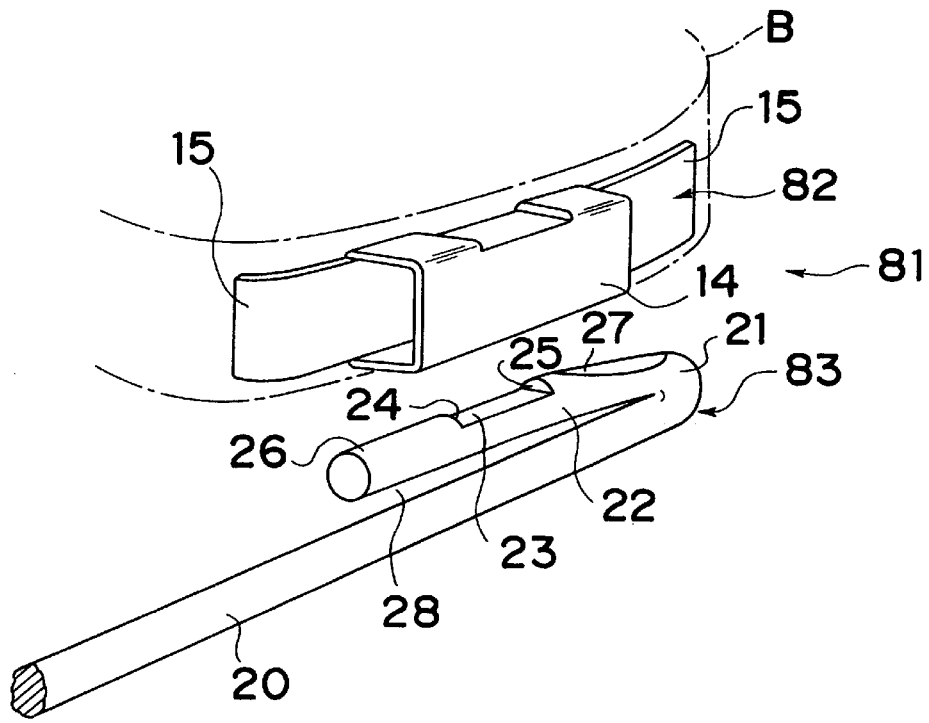
FIG. 10 is a perspective view of an embodiment 7 of the lock for orthodontic treatment of the invention in disengaged condition.
Figure 11:
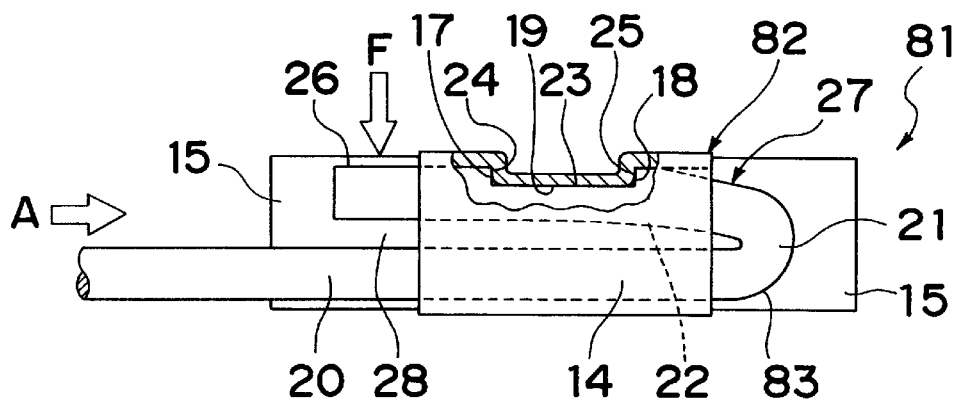
FIG. 11 is a front view of the lock shown in FIG. 10 in engaged condition.

FIGS. 10 and 11 illustrate a lock 81 representing a seventh embodiment of the invention. In this embodiment, an inwardly projecting engagement surface portion 19 is formed on the upper wall of the tubular portion 14 of a holding tube 82, and opposite end edges of the engagement surface portion 19 act as engaging edges 17, 18. A spring hook portion 22 of a spring wire 83 is formed with a cutout surface portion 23 engageable with the engagement surface portion 19 of the tubular portion 14, and opposite ends of the cutout surface portion 23 act as end edges 24, 25.

When the spring wire 83 is inserted into the tubular portion 14 in the direction of arrow A, the cutout surface portion 23 of the spring hook portion 22 comes into engagement with the engagement surface portion 19 of the tubular portion 14. As a result, the end edge 24 of the spring wire 83 engages with the engaging edge 17 of the tubular portion 14 so that the wire movement in the inserting direction is prevented, and the end edge 25 of the spring wire 83 engages with the engaging edge 18 of the tubular portion 14 so that the wire movement in the removing direction is prevented. For removing the spring wire 83, as in the case of the foregoing embodiment, an outer end portion 26 or curved portion 21 of the spring hook portion 22 which projects from one end of the tubular portion 14 is pressed in the direction of arrow F. Thereby, the cutout surface portion 23 of the spring hook portion 22 is disengaged from the engagement surface portion 19 of the tubular portion 14. Thus, the spring wire 83 can be pulled out of the tubular portion 14. In this embodiment, the tubular portion 14 has no opening other than the openings at opposite ends, such as window 16 in the above described embodiment. Therefore, the device has smooth outer surface and high strength characteristic.

Figure 12:
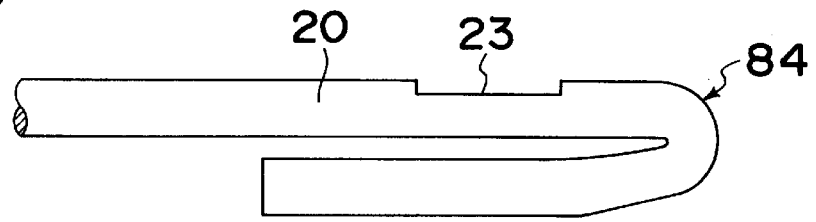
FIG. 12 is a front view of a modified form of the spring wire of the lock shown in FIG. 10.

In place of the spring wire 83 shown in FIGS. 10 and 11, a spring wire 83 having a cutout surface portion 23 formed on a wire body 20 as shown in FIG. 12 may be used.

Embodiment 8

Figure 13A:
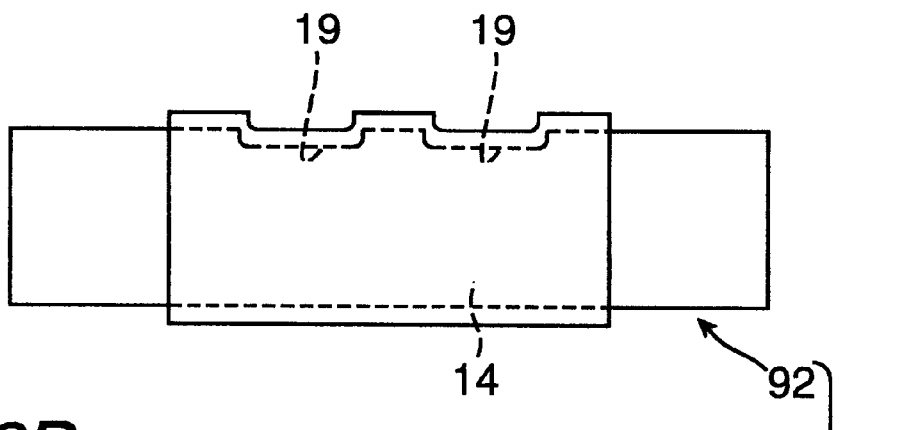
FIGS. 13A and 13B are front views of a holding tube and a spring wire, respectively, in an embodiment 8 of the lock of the invention.
Figure 13B:
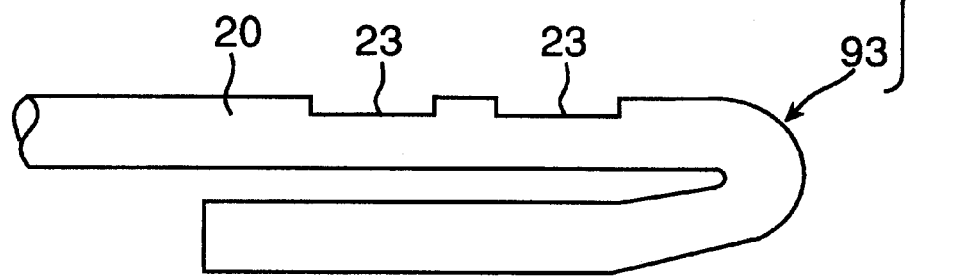
Figure 13C:
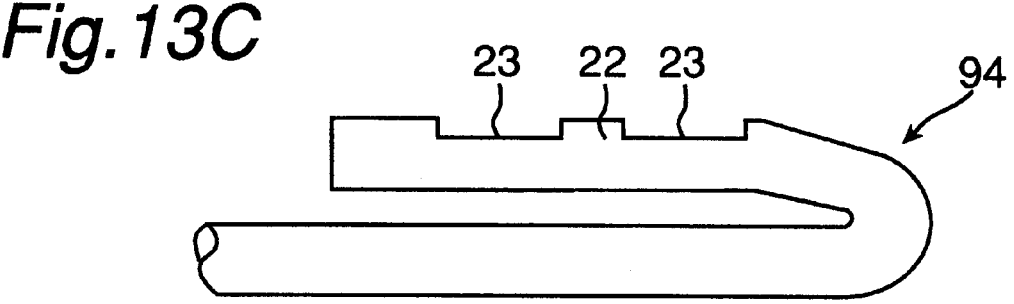
FIG. 13C is a front view of a modified form of the spring wire shown in FIG. 13B.

FIGS. 13A and 13B show respectively a holding tube 92 and a spring wire 93 of a lock 91 representing an eighth embodiment of the invention. In this eighth embodiment, a tubular portion 14 of the holding tube 92 has two engagement surface portions 19 formed thereon which are similar to those in the seventh embodiment shown in FIGS. 10 and 11, and two cutout surface portions 23 engageable with the engagement surface portions 19 are formed on the wire body 20 of the spring wire 93. The eighth embodiment provides more powerful locking performance than the seventh embodiment. In stead of the spring wire 93 as shown in FIG. 13C, a spring wire 94 having two cutout surface portions 23 formed on a spring hook portion 22 as shown in FIG. 13C may be used.

Embodiment 10

Figure 19A:
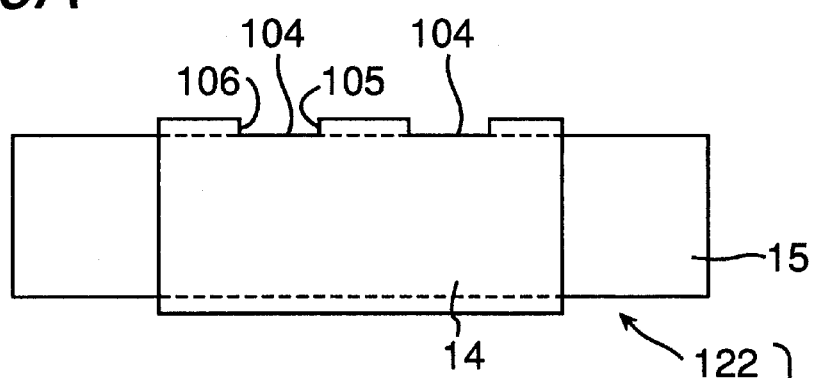
FIGS. 19A and 19B are front views of a holding tube and a spring wire, respectively, in an embodiment 10 of the lock for orthodontic treatment of the invention.
Figure 19B:
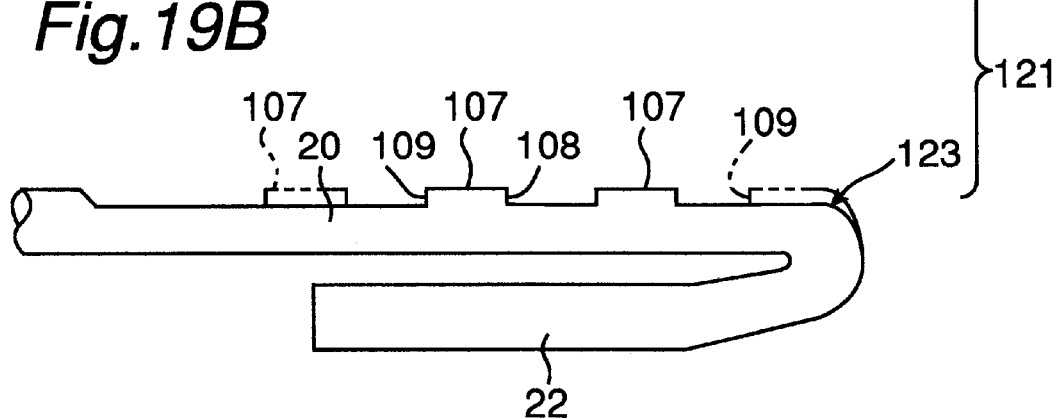

FIGS. 19A and 19B show a holding tube 92 and a spring wire 123, respectively, of a lock 121 representing a tenth embodiment of the invention. In this tenth embodiment, the holding tube 12 is formed with two engagement hole portions 104 similar to the engagement hole portion in the ninth embodiment shown in FIGS. 9 and 10, while the wire body 20 of the spring wire 123 is formed with two engagement raised portions 107 engageable with the engagement hole portions 104. This eighth embodiment provides more powerful locking effect than the seventh embodiment. In this tenth embodiment, it is basically intended that the two engagement raised portions 107 come into engagement with the two engagement hole portions 104. However, the engagement raised portion 107 shown at left side may engage with the engagement hole portion 104 shown at right side, or the engagement raised portion 107 shown at right side may engage with the engagement hole portion 104 shown at left side. In this way, the spring wire 123 can be locked at any one of three positions. Therefore, this enables length adjustment of the wire spring 123 in clinical use of the device.

Where a projection 109 is formed ahead of the engagement raised portion 107 located at the fore side of the wire body 20 so that the projection 109 can come into engagement with one end edge of the holding tube 122, possible slip off can be reliably prevented.

As shown by a phantom line in FIG. 19B, the wire body 20 may be provided with another engagement raised portion 107. This enables the locking position of the spring wire to be adjusted in two steps, namely, a first step for engaging two fore-side engagement raised portions 107, 107 of the wire body 20 with the engagement hole portions 104, 104 of the holding tube 122, and a second step for engaging two hindside engagement raised portions 107, 107 of the wire body 20 with the engagement hole portions 104, 104 of the holding tube 122. Conversely, engagement hole portions 104 of the holding tube 12 may be provided in three or more in number.

Figure 19C:
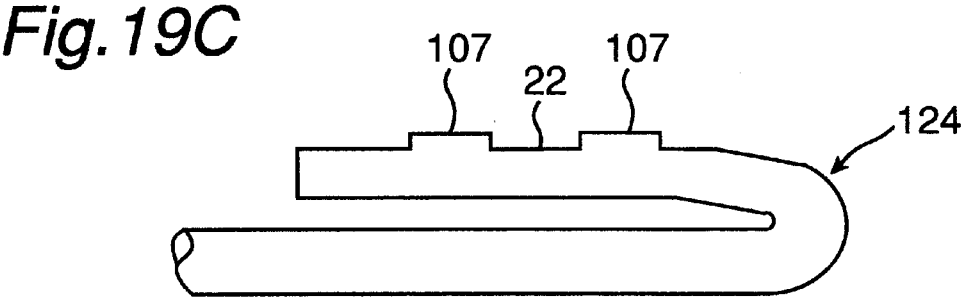
FIG. 19C is a front view of a modified form of the spring wire shown in FIG. 19B.

In place of the spring wire 123, a spring wire 124 having two engagement raised portion s 107 formed in the spring hook portion 22, as shown in FIG. 19C, may be used.

Embodiment 11

Figure 14:
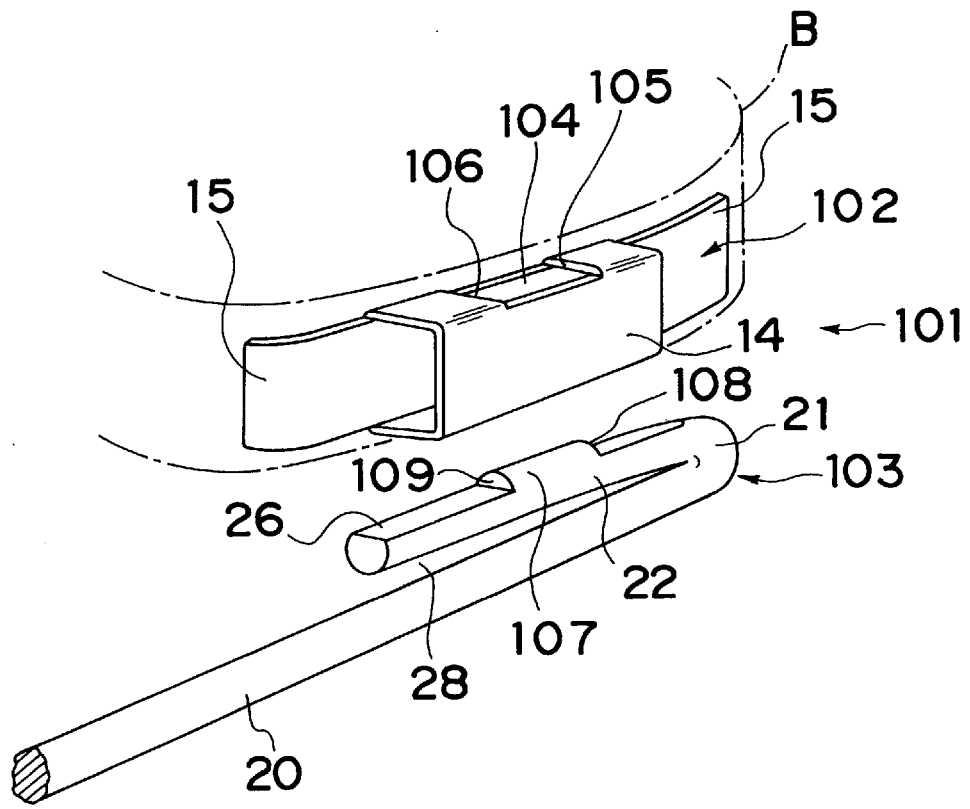
FIGS. 14a and 14b are front views of a holding tube and a spring wire, respectively, in an embodiment 30 of the lock for orthodontic treatment of the invention.
Figure 15:
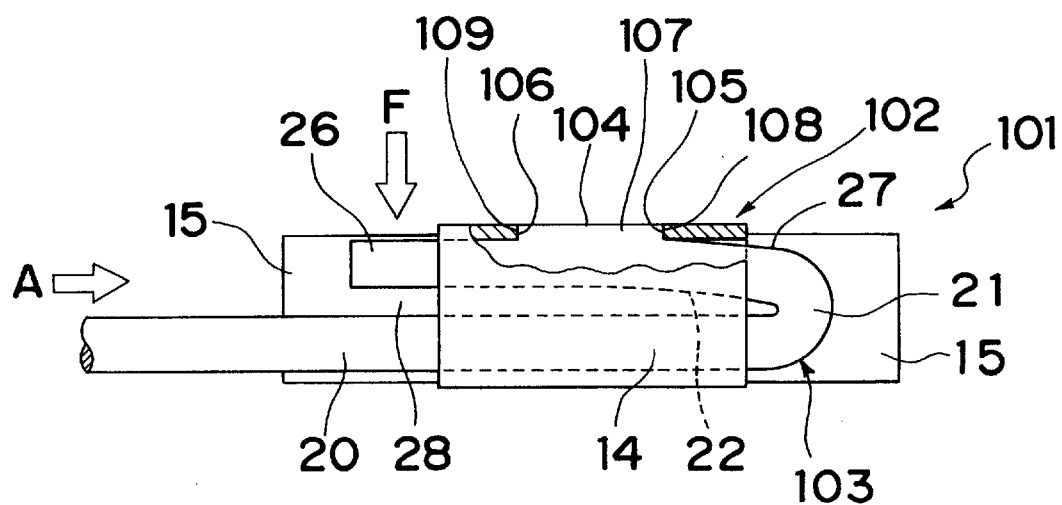
FIG. 15 is a perspective view of an embodiment 31 of the lock for orthodontic treatment of the invention in disengaged condition.
Figure 20:
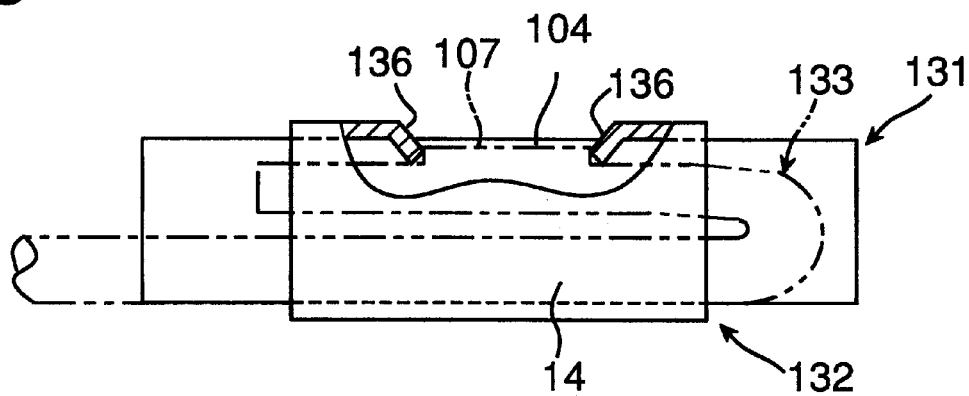
FIG. 20 is a front view of a holding tube in an embodiment 11 of the lock for orthodontic treatment of the invention.
Figure 21:
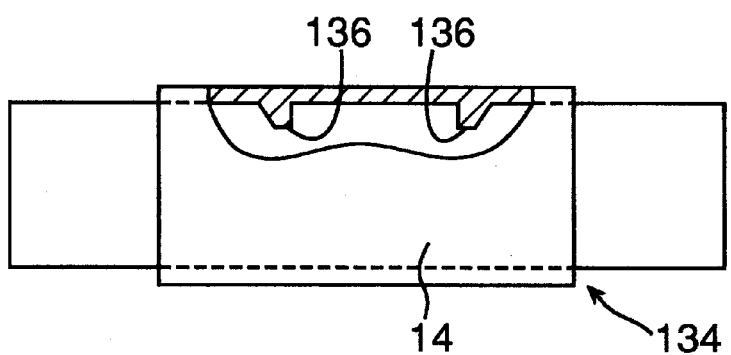
FIG. 21 is a front view of a modified form of the holding tube shown in FIG. 20.
Figure 22:
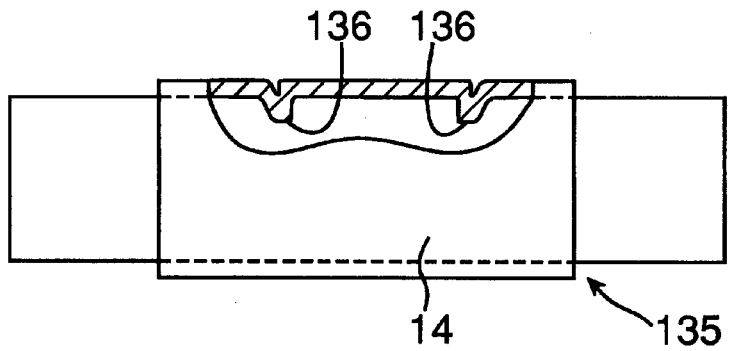
FIG. 22 is a front view of an another modified form of the holding tube shown in FIG. 20.

FIGS. 20 to 22 illustrate holding tubes 132, 134, 135 of a lock 131 representing an eleventh embodiment of the invention. In these holding tubes 132, 134, 135, a pair of inwardly projecting projections 136 are formed on the inner surface of upper wall of the tubular portion 14 so that the pair of projections 136 serve as engaging edges. Projections 136 of the holding tube 132 shown in FIG. 20 are formed by inwardly bending opposite end edges of an engagement hole portion 104 formed in the tubular portion 14. Projections 136 of the holding tube 134 shown in FIG. 21 are formed by securely fixing a small piece to or depositing a noble metal solder on the interior surface of the upper wall of the tubular portion 14. Projections 136 of the holding tube 135 shown in FIG. 22 are formed by depressing the outer surface of upper wall of the tubular portion 14. The spring wire 133 inserted into such holding tube 132, 134, 135, as described with respect to the ninth embodiment shown in FIGS. 14 and 15, is formed with an engagement raised portion 107 to be held between a pair of projections 136. The locking function of these arrangement is same as what has been described with respect to the foregoing embodiment.

Embodiment 12

Figure 23:
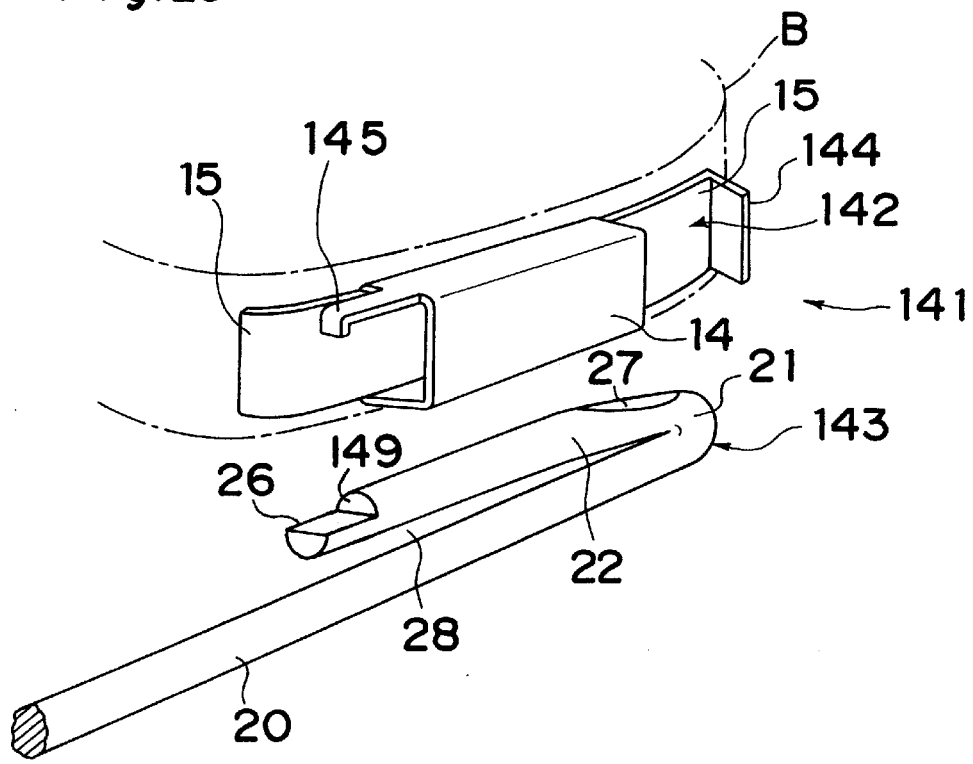
FIG. 23 is a perspective view of an embodiment 12 of the lock for orthodontic treatment of the invention in disengaged condition.
Figure 24:
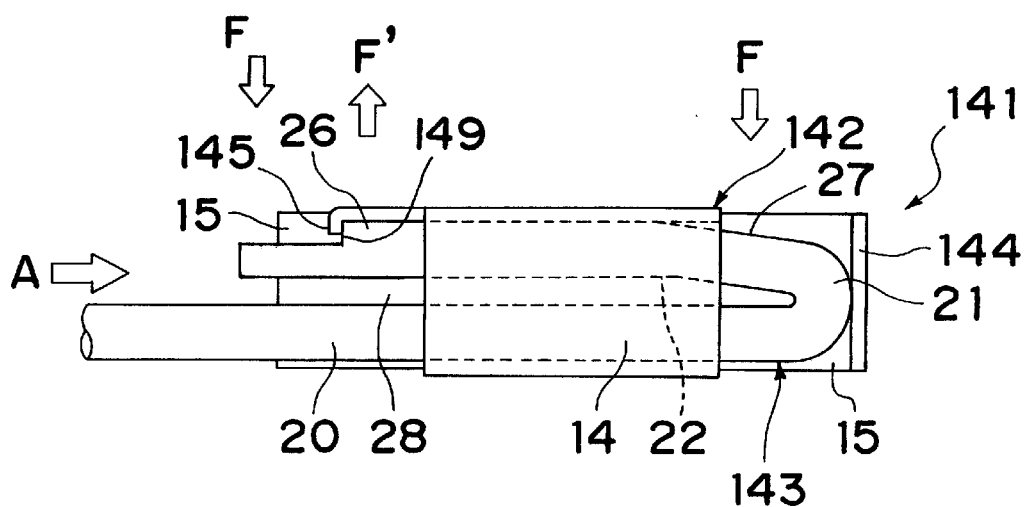
FIG. 24 is a front view of the lock shown in FIG. 23 in engaged condition.

FIGS. 23 and 24 show a lock 141 representing a twelfth embodiment of the invention. In this embodiment, a holding tube 14 includes a bent edge 144, as a first engaging portion, formed by bending perpendicularly to the axis the forward end of a wing portion 15 extending axially from one end of the tubular portion 14 of a holding tube 142, and an elastic pawl projection 145, as a second engaging portion, extending axially from the upper wall of other end of the tubular portion 14 and projecting perpendicularly to the axis. The pawl projection 145 may be made shorter and non-elastic by bending the edge of the tubular portion 14. A fore-side end of the spring hook portion 22 of the spring wire 143 is notched to define a stepped projection 149. In the spring wire 143, the outer surface of its curved portion 21 and the projection 149 respectively form end edges for coming into engagement with the bent piece 144 and the pawl projection 145.

When the spring wire 143 is inserted into the tubular portion 14 in the direction of arrow A, the outer surface of the curved portion 21 of the spring hook portion 22 abuts the bent edge 144 of the tubular portion 14 and, simultaneously therewith, the projection 149 of the spring hook portion 22 is engaged by the pawl projection 145. As a result, movement of the spring wire 143 in the inserting direction as well as in the removing direction is prevented. For removing the spring wire 143, the outer end portion 26 of the spring hook portion 22 is depressed in the direction of arrow F, or the pawl projection 145 is pulled up in the direction of arrow F', or the curved portion 21 of the spring hook portion 22 projecting from one end of the tubular portion 14 is depressed in the direction of arrow F. As a result, the projection 149 of the spring hook portion 22 is disengaged from the pawl projection 145 of the tubular portion 14 and thus the spring wire 143 can be pulled out of the tubular portion 14.

In the above described twelfth embodiment, a stepped projection 156 is formed at the fore side end of the spring hook portion 22. As an alternative, the end surface of the fore side end portion of the spring hook portion 22 may be adapted to be engaged by the pawl projection 145. In this arrangement, it is unnecessary to provide the spring wire 143 with projection 149, cutout surface portion 23, engagement hole portion 76, engagement raised portion 107, or the like. Therefore, the device presents smooth outer surface and good service characteristics, and is inexpensive to fabricate.

Figure 25:
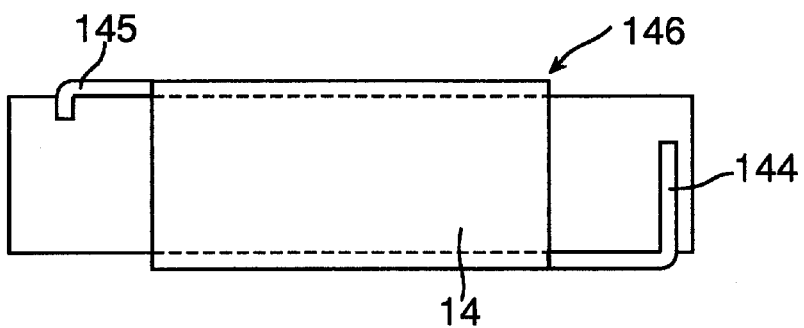
FIG. 25 is a front view of a modified form of the holding tube of the lock shown in FIG. 23.
Figure 26:
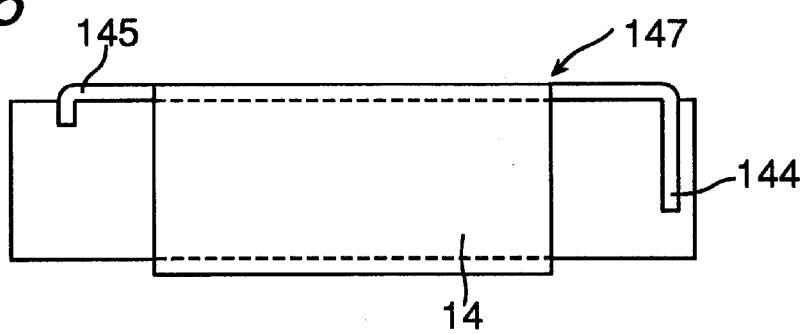
FIG. 26 is a front view of an another modified form of the holding tube of the lock shown in FIG. 23.
Figure 27:
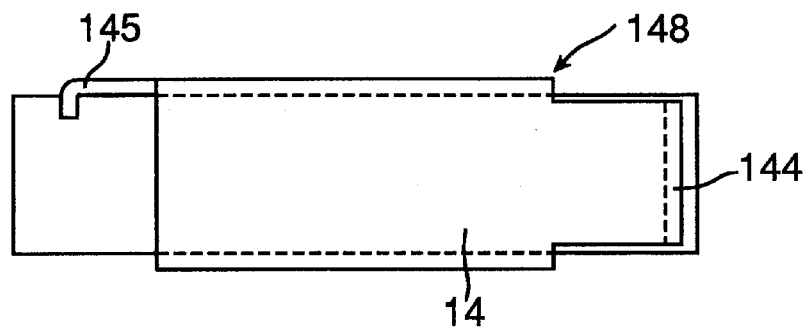
FIG. 27 is a front view of a still another modified form of the holding tube of the lock shown in FIG. 23.

In the above described twelfth embodiment, the bent edge 144 is formed at the wing portion 15. However, as exemplified by holding tubes 146, 147, 148 shown in FIGS. 25, 26, 27, such a bent edge may be provided as an extension from a bottom wall, an upper wall, or a front wall at one end of the tubular portion 14.

Embodiment 13

Figure 28A:
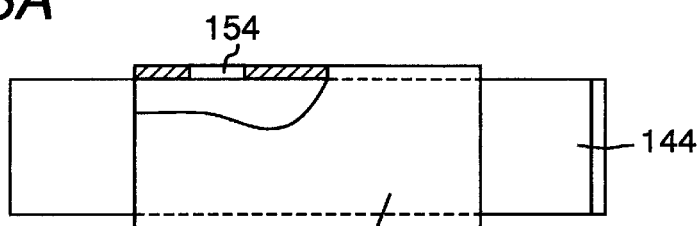
FIGS. 28A and 28B are front views of a holding tube and a spring wire, respectively, in an embodiment 13 of the lock for orthodontic treatment of the invention.
Figure 28B:
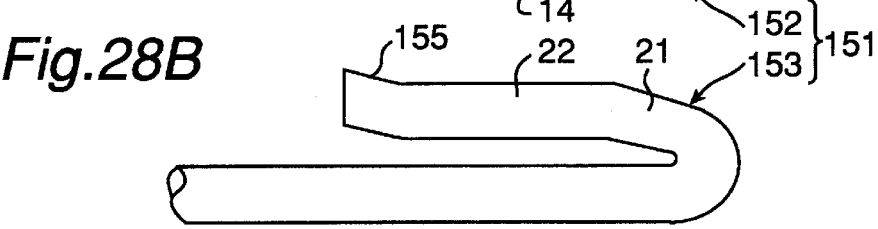

FIGS. 28A and 28B show a holding tube 152 and a spring wire 153 respectively of a lock 151 representing a thirteenth embodiment of the invention. In this thirteenth embodiment, a bent edge 144 similar to the bent edge 144 of the twelfth embodiment shown in FIGS. 23 and 24 is formed at one end of the holding tube 152, and a hole portion 154 is formed in an upper wall in the proximity of other end of the holding tube 152. The spring wire 153 is formed at fore side end of the spring hook portion 22 with an outwardly flexing bent portion 155.

When the spring wire 153 is inserted into the tubular portion 14, the outer surface of the curved portion 21 of the spring hook portion 22 abuts the bent edge 144 of the tubular portion 14 and, simultaneously therewith, the tip end corner of the bent portion 155 of the spring hook portion 22 engages with the hole portion 154. As a result, movement of the spring wire 153 in the inserting direction as well as in the removing direction is prevented. To remove the spring wire 153, the tip end corner of the bent portion 155 of the spring hook portion 22 is pushed inward from outside the hole portion 154 by using a pin or the like, or the curved portion 21 of the spring hook portion 22 projecting from one end of the tubular portion 14 is depressed. As a result, the tip end corner of the spring hook portion 22 is disengaged from the hole portion 154 of the tubular portion 14 and thus the spring wire 153 can be pulled out of the tubular portion 14.

Figure 28C:
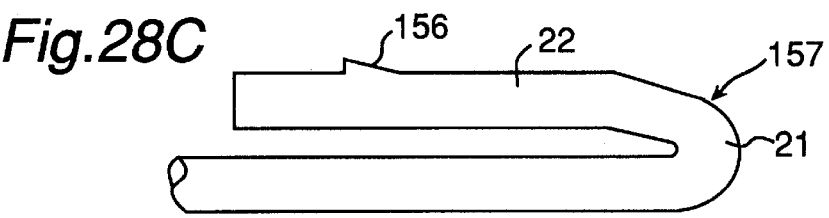
FIGS. 28C–F are front views of modified forms of the spring wire shown in FIG. 28B.
Figure 28D:
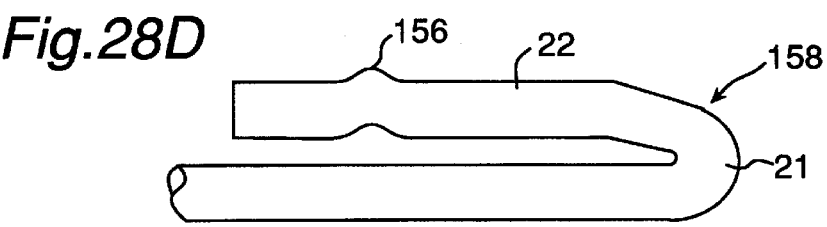
Figure 28E:
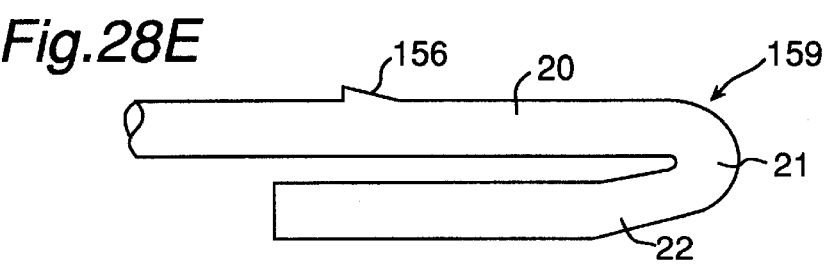
Figure 28F:
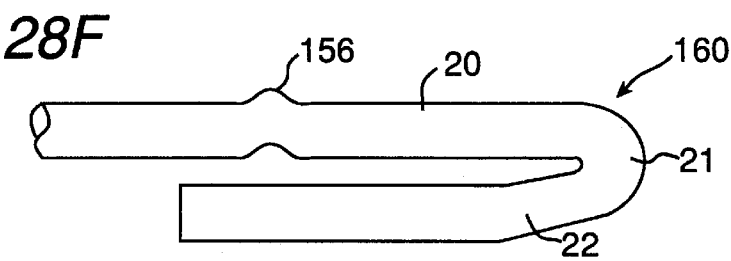

Instead of the spring wire 153, a spring wire 157 as shown in FIG. 28C may be used which has a projection 156 formed adjacent the tip end corner of the spring hook portion 22 which is engageable with the hole portion 154 of the tubular portion 14. The projection 156 can be formed by fixing s small-piece or soldering noble metal. Also, as exemplified by a spring wire 158 shown in FIG. 28D, it is possible to form a projection 156 by press bending. Further, a spring wire 159, 160 as shown in FIGS. 28E and 28F may be used which has a projection 156 formed on a wire body 20 opposed to the spring hook portion 22.

Embodiment 14

Figure 29A:
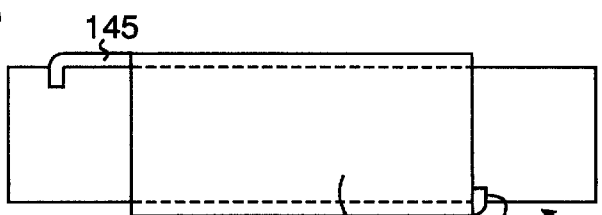
FIGS. 29A and 29B are front views of a holding tube and a spring wire, respectively, in an embodiment 14 of the lock for orthodontic treatment of the invention.
Figure 29B:
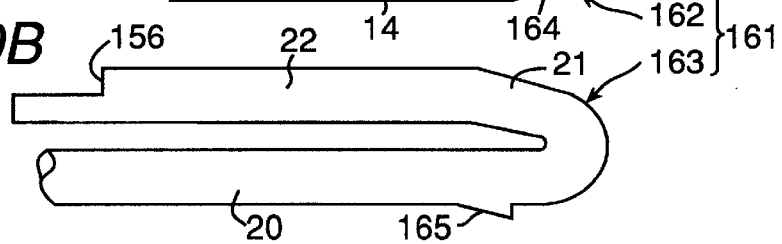

FIGS. 29A and 29B show a holding tube 162 and a spring wire 163, respectively, of a lock 161 representing a fourteenth embodiment of the invention. In this fourteenth embodiment, the holding tube 162 includes a pawl portion 164 projecting inwardly from the lower wall of one end edge of the tubular portion 14, and an elastic pawl projection 145 extending axially from the upper wall of other end of the tubular portion 14 and projecting inwardly perpendicularly to the axis. The spring wire 163 includes a stepped projection 156 formed adjacent the tip end of the spring hook portion 22, and a projection 165 formed on the wire body 20 opposed to the spring hook portion 22.

When the spring wire 163 is inserted into the tubular portion 14, the projection 165 of the wire body 20 is engaged by the pawl portion 164 of the tubular portion 14, and simultaneously therewith, the projection 156 of the spring hook portion 22 is engaged by the pawl projection 145. As a result, movement of the spring wire 163 in the inserting direction as well as in the removing direction is prevented. To remove the spring wire 163, the pawl portion 145 is pulled up, or the curved portion 21 of the spring hook portion 22 projecting from one end of the tubular portion 14 is depressed. As a result, the projection 156 at the tip end of the spring hook portion 22 is disengaged from the pawl projection 145 of the tubular portion 14 and thus the spring wire 163 can be pulled out of the tubular portion 14.

In the above described fourteenth embodiment, the spring hook portion 22 has a stepped projection 156 formed at its tip end portion. As an alternative, it may be arranged that the tip end of the spring hook portion 22 is engaged by the pawl projection 145.

Figure 29C:
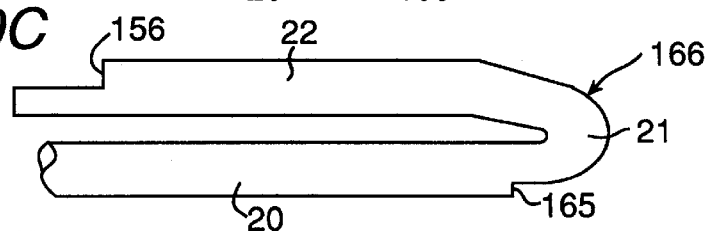
FIGS. 29C–G are front views of modified forms of the spring wire shown in FIG. 29B.
Figure 29D:
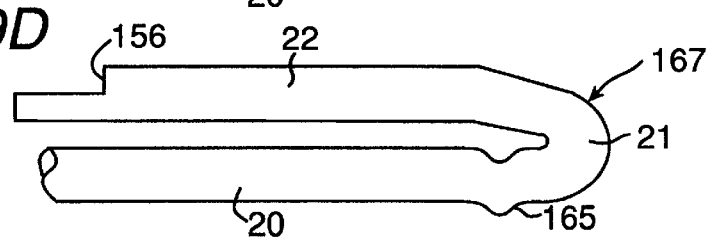
Figure 29E:
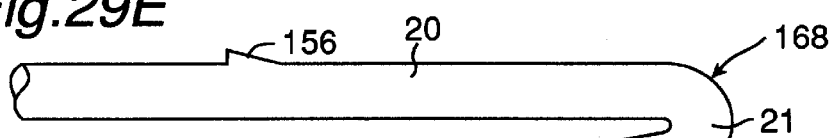
Figure 29F:
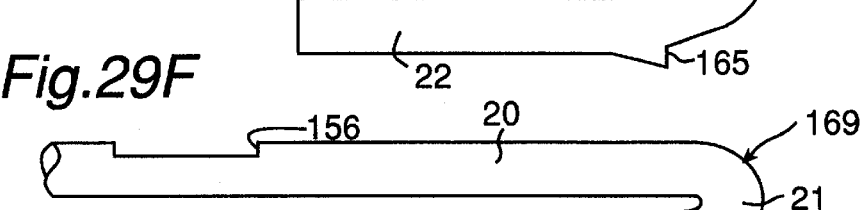
Figure 29G:
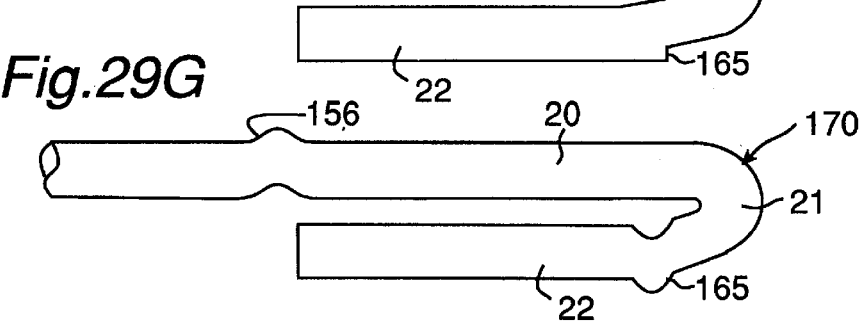
Figure 30A:
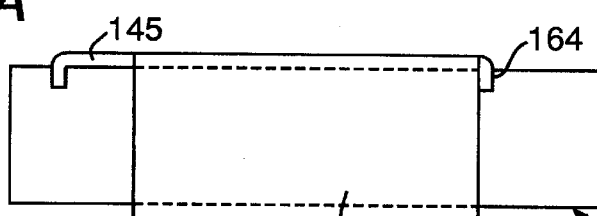
FIGS. 30A and 30B are front views of a holding tube and a spring wire, respectively, in an embodiment 15 of the lock for orthodontic treatment of the invention.
Figure 30B:
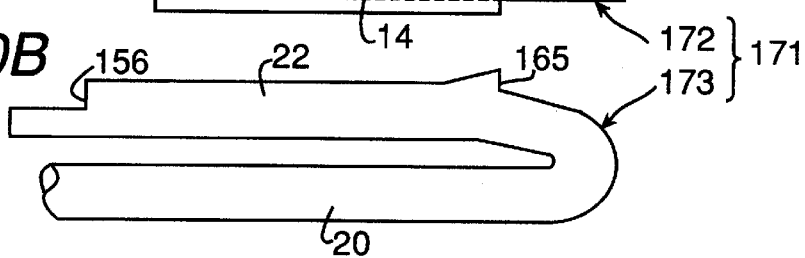
Figure 30C:
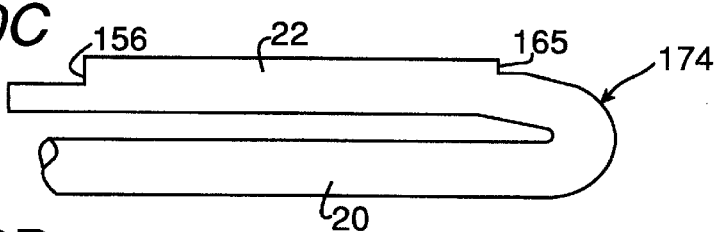
FIGS. 30C–G are front views of modified forms of the spring wire shown in FIG. 30B.
Figure 30D:
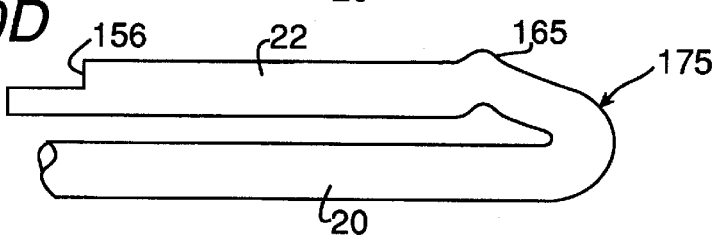
Figure 30E:
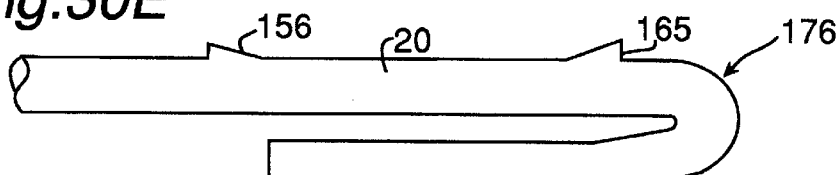
Figure 30F:
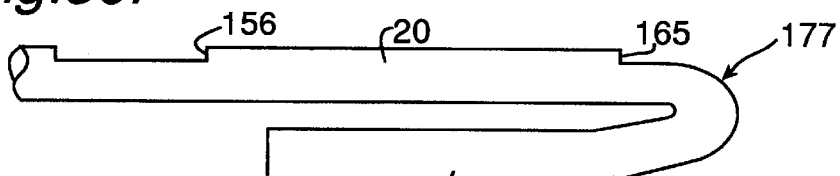
Figure 30G:
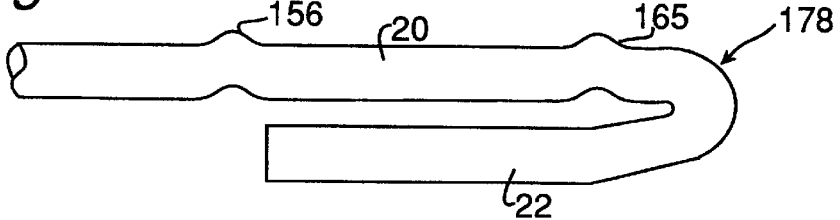
Figure 31A:
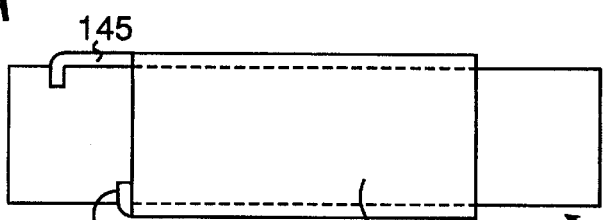
FIGS. 31A and 31B are front views of a holding tube and a spring wire, respectively, in an embodiment 16 of the lock for orthodontic treatment of the invention.
Figure 31B:
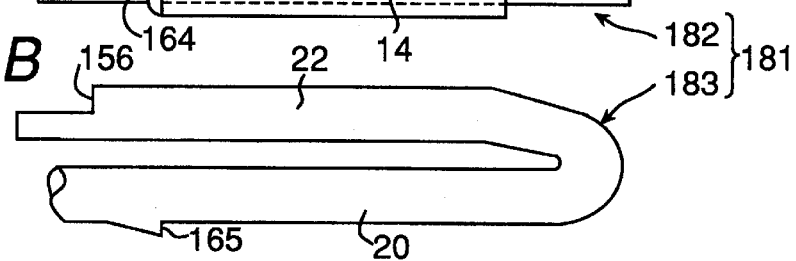
Figure 31C:
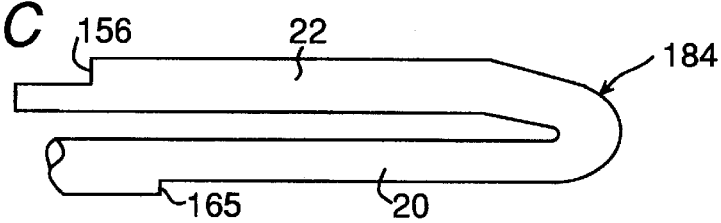
FIGS. 31C–G are front views of modified forms of the spring wire shown in FIG. 31B.
Figure 31D:
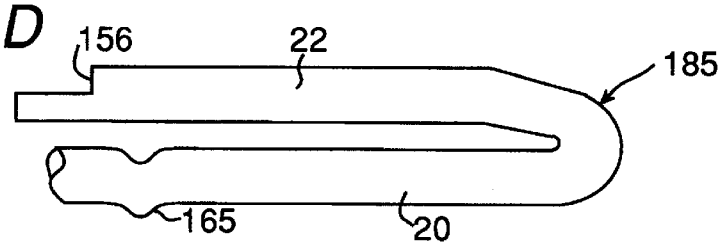
Figure 31E:
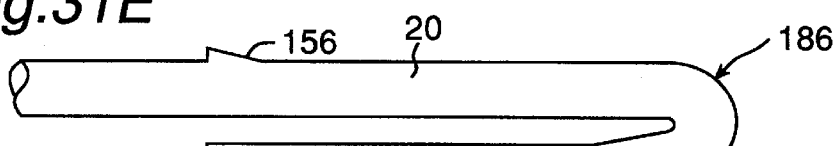
Figure 31F:
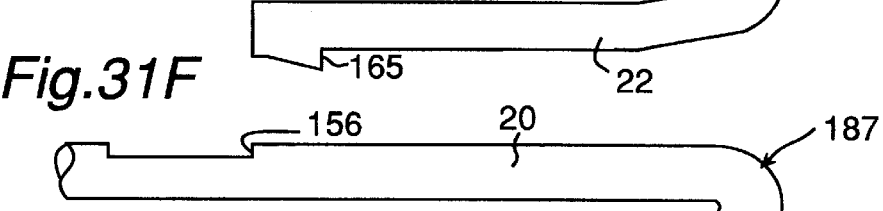
Figure 31G:
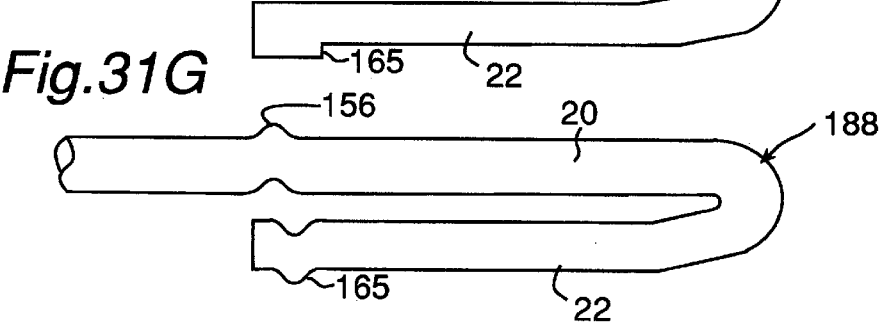

As an alternative to the spring wire 163, it is possible to use a spring wire 166 having a stepped projection 165 formed by cutting off a portion adjacent the curved portion 21 of the wire body 20 as shown in FIG. 29C, or a spring wire 167 having a projection 165 formed by bending as shown in FIG. 29D. Also, it is possible to use a spring wire 168, 169, 170 as shown in FIGS. 29E through 29G in which a projection 165 engageable with a pawl portion 164 of the tubular portion 14 is formed on the spring hook portion 22, and a projection 156 engageable with a pawl projection 145 of the tubular portion 14 is formed on the wire body 20.

Embodiment 15

FIGS. 30A through 30G illustrate a holding tube 172 and a spring wire 173 of a lock 171 representing a fifteenth embodiment of the invention and illustrate modified forms of the spring wires 174–178. In this fifteenth embodiment, a pawl portion 164 corresponding to that in the fourteenth embodiment shown in FIGS. 29A and 29B is provided at one end of the upper wall of the tubular portion 14. The locking function in the fifteenth embodiment is same as that in the fourteenth embodiment.

Embodiment 16

FIGS. 31A through 31G illustrate a holding tube 182 and a spring wire 183 of a lock 181 representing a sixteenth embodiment of the invention and illustrate modified forms of the spring wires 184–188. In this sixteenth embodiment, a pawl portion 164 corresponding to that in the fourteenth embodiment shown in FIGS. 29A and 29B is provided at inlet side end edge of the tubular portion 14. The locking function in the sixteen embodiment is same as that in the fourteenth embodiment. In this sixteenth embodiment, the pawl portion 164 need not necessarily be provided and the inlet-side end edge per se may be made to serve as a first locking portion.

It is noted that in the fourteenth and fifteenth embodiments, a hole portion 154 as in the thirteenth embodiment may be provided in place of the pawl projection 145.

Embodiment 17

In the foregoing first to sixteenth embodiments, the spring wire includes a spring hook portion 22 having elastic characteristics, but in the seventeenth to twenty-fifth embodiments to be described hereinafter, the spring wire has no elastic characteristics, whereas the holding tube has elastic characteristics.

Figure 32:
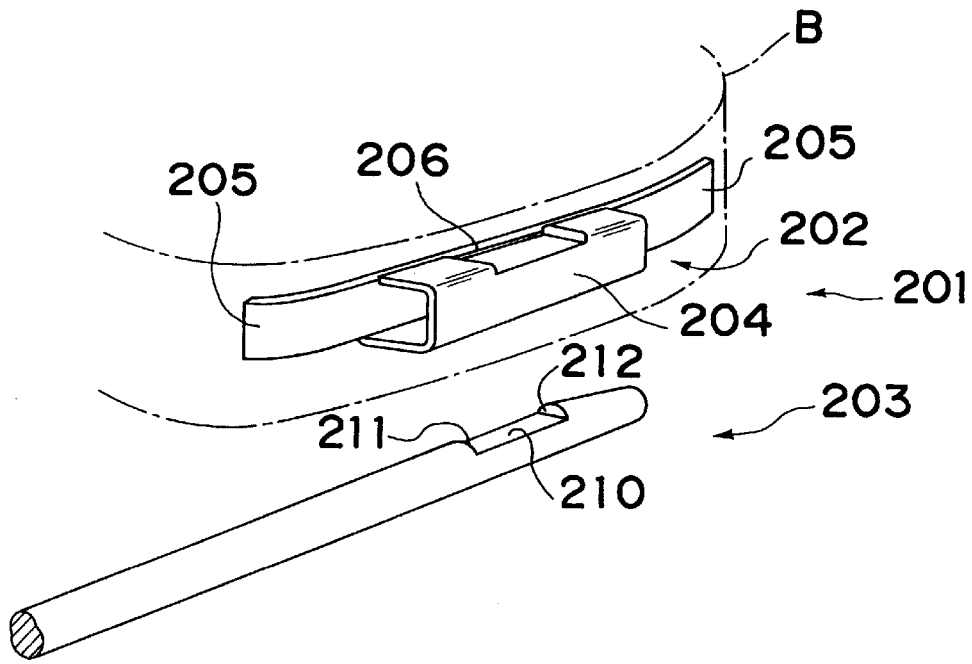
FIG. 32 is a perspective view of an embodiment 17 of the lock for orthodontic treatment of the invention in disengaged condition.
Figure 33:
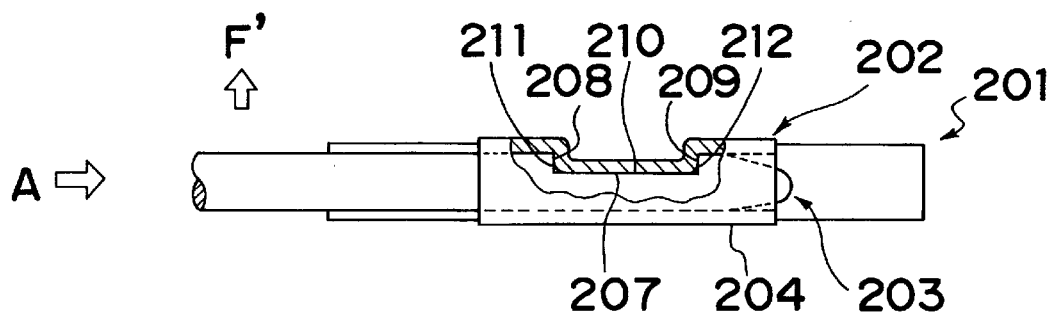
FIG. 33 is a front view of the lock shown in FIG. 32 in engaged condition.
Figure 35:
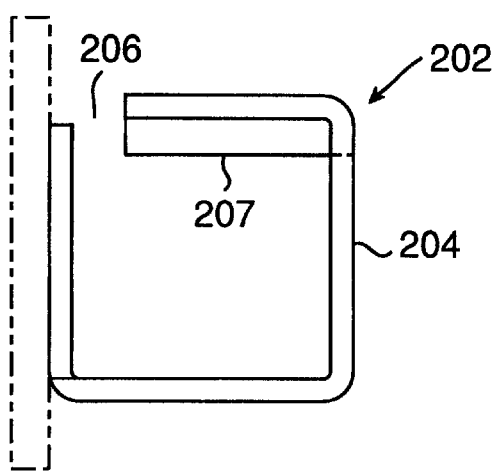
FIG. 35 is a left side view of the holding tube of the lock shown in FIG. 32.

FIGS. 32 and 33 illustrate a lock representing a seventeenth embodiment of the invention. In this embodiment, a holding tube 202 includes a tubular portion 204 having a rectangular section of which one side is slightly larger than the outer dimension of the spring wire 203, and wing portions 205 extending laterally from opposite ends of a rear side wall of the tubular portion 204. The tubular portion 204, as FIG. 35 shows, has an axially extending slit 206 formed along a corner portion defined by the rear side wall and an upper wall, whereby the tubular portion is possessed of elastic characteristics effective in the direction perpendicular to the axis. The tubular portion 204 has an inwardly projecting engagement surface portion 207 formed on its upper wall, and opposite end edges of which serve as engaging edges 208, 209. The spring wire 203 is formed on the upper surface of a straight end portion thereof with a cutout surface portion 210, opposite ends of which serve as end edges 211, 212.

When the spring wire 203 is inserted into the tubular portion 204 in the direction of arrow A, the engagement surface portion 207 of the tubular portion 204 is pressed by the distal end of the spring wire 203 so that the tubular portion 204 is expanded. When the spring wire 203 is inserted further until the cutout surface portion 210 of the spring wire 203 coincides with the engagement surface portion 207 of the tubular portion 204, the tubular portion 204 is contracted by its own elasticity so that the engagement surface portion 207 of the tubular portion 204 comes into engagement with the cutout surface portion 210 of the spring wire 203. As a result, an end edge 211 of the spring wire 203 is engaged by an engaging edge 208 of the tubular portion 204 so that the spring wire is prevented from further movement in the inserting direction. At the same time, the end edge 211 of the spring wire 203 is engaged by the engaging edge 208 of the tubular portion 204 so that the spring wire is prevented from movement in the removing direction.

To remove the spring wire 203, the spring wire 203 is lifted in the direction of arrow F', or a suitable tool is inserted in the slit 206 to pull up the upper wall portion 204. As a result, the upper wall of the tubular portion 204 is forced upward to cause the engagement surface portion 207 of the tubular portion 204 to be disengaged from the cutout surface portion 210 of the spring wire 203. Thus, the spring wire 203 can be drawn out of the tubular portion 204. In this embodiment, the tubular portion 204 is of a small size such that it is substantially equal to the diameter of the spring wire 203. Therefore, the device is particularly suitable for use in the case where the crown length is short. Both holding tube 202 and the spring wire 203 are simple in configuration, easy to fabricate, and inexpensive.

Figure 34:
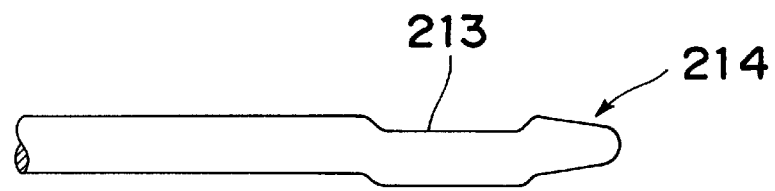
FIG. 34 is a front view of a modified form of the spring wire of the lock shown in FIG. 32.
Figure 36:
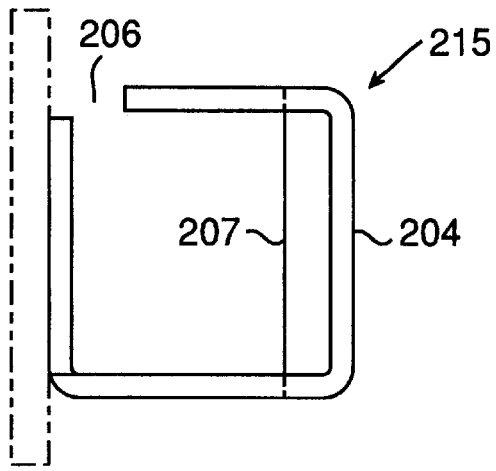
FIG. 36 is a left side view of a modified form of the holding tube shown in FIG. 35.
Figure 37:
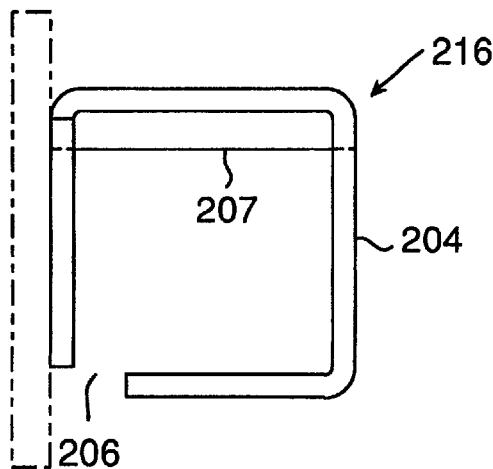
FIG. 37 is a left side view of an another modified form of the holding tube shown in FIG. 35.
Figure 37A:
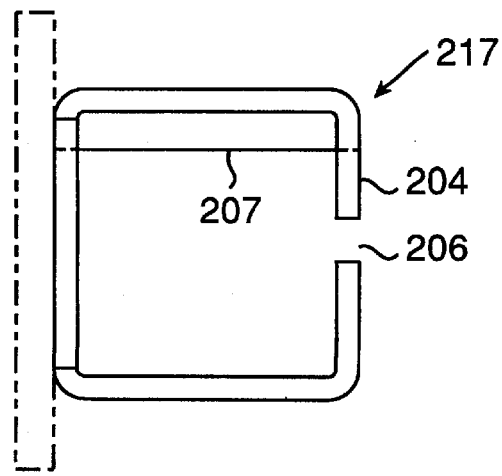
FIG. 37A is a left side view of a still another modified form of the holding tube shown in FIG. 35.

In the above described seventeenth embodiment, it is possible to use, as an alternative to the spring wire 203 with the cutout surface portion 210, a spring wire 214 having an engagement recess portion 213 formed by bending as shown in FIG. 34. The engagement surface portion 207 of the tubular portion 204 may be formed on a front wall as in the case of a holding tube 215 shown in FIG. 36. The slit 206 of the tubular portion 204 may be provided in a corner portion defined by the rear side wall and the lower wall as in the case of a holding tube 216 shown in FIG. 37, or may be provided centrally of the front wall as in the case of a holding tube 217 shown in FIG. 37A.

A crushed portion 26a as shown in FIG. 1A may be provided at a location spaced at least the length of the tubular portion 204 of the holding tube 202 or more from the tip of the spring wire 203 in the seventeenth embodiment, whereby the spring wire 203 can be prevented from projecting through the holding tube 202 during the inserting process of the spring wire 203.

Embodiment 18

Figure 38A:
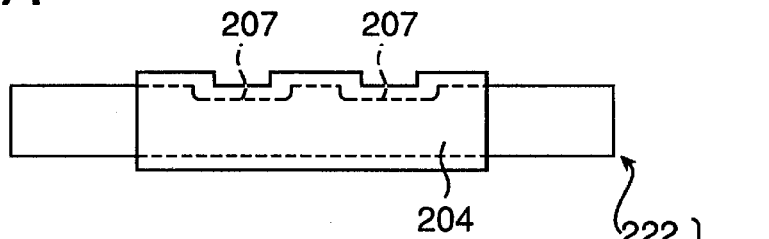
FIGS. 38A and 38B are front views of a holding tube and a spring wire, respectively, in an embodiment 18 of the lock for orthodontic treatment of the invention.
Figure 38B:
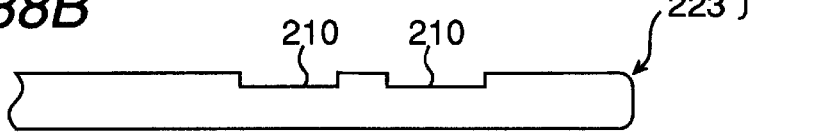

FIGS. 38A and 38B illustrate a holding tube 222 and a spring wire 223, respectively, of a lock 221 according to an eighteenth embodiment of the invention. In this eighteenth embodiment, the holding tube 222 is formed with two engagement surface portions 207 which are similar to the engagement surface portion 207 in the seventeenth embodiment shown in FIGS. 32 and 32, while the spring wire 223 is formed with two cutout surface portions 210 engageable with the engagement surface portions 207. This embodiment provides more powerful locking effect than the seventeenth embodiment.

Embodiment 19

Figure 39A:
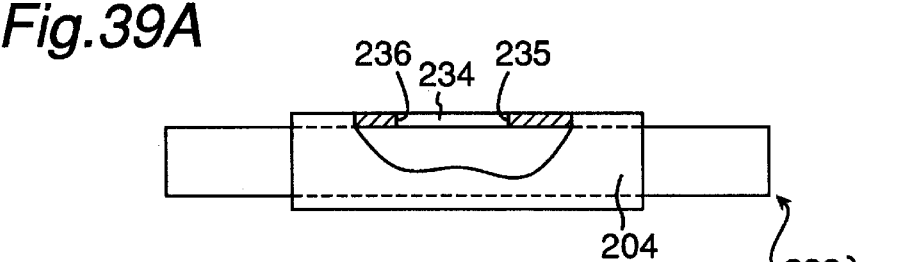
FIGS. 39A and 39B are front views of a holding tube and a spring wire, respectively, in an embodiment 19 of the lock for orthodontic treatment of the invention.
Figure 39B:
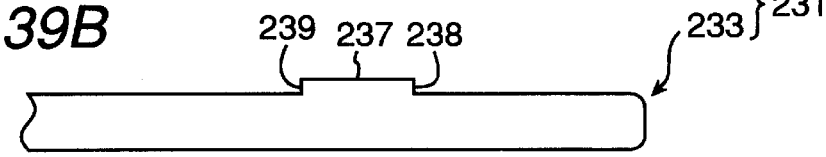

FIGS. 39A and 39B illustrate a holding tube 232 and a spring wire 233, respectively, of a lock 231 according to a nineteenth embodiment of the invention. In this embodiment, an engagement hole portion 234 is formed in the upper wall of the tubular portion 204, and opposite end edges of which serve as engaging edges 235, 236. The spring wire 233 is formed with an engagement raised portion 237 engageable with the engagement hole portion 234, and opposite ends of which serve as end edges 238, 239. This embodiment is such that engagement hole portion 234 and engagement raised portion 237 are provided, respectively, in place of the engagement surface portion 207 of the tubular portion 204 and the cutout surface portion 210 of the spring wire 203 in the seventeenth embodiment shown in FIGS. 32 and 33. The locking function of these elements are same as that in the seventeenth embodiment. The engagement raised portion 237 of the spring wire 233 shown in FIG. 39B may be formed by bending as shown in FIG. 34.

Embodiment 20

Figure 40A:
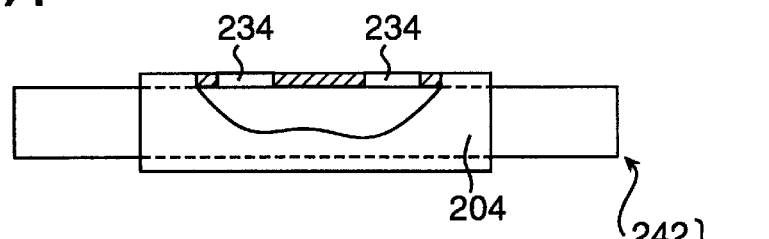
FIGS. 40A and 40B are front views of a holding tube and a spring wire, respectively, in an embodiment 20 of the lock for orthodontic treatment of the invention.
Figure 40B:
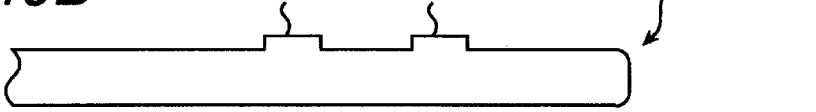

FIGS. 40A and 40B illustrate a holding tube 242 and a spring wire 243, respectively, of a lock 241 according to a twentieth embodiment of the invention. This embodiment is such that the holding tube 242 has formed therein two engagement hole portions 234 similar to the engagement hole portion 234 in the nineteenth embodiment shown in FIG. 39A, while the spring wire 234 has formed thereon with two engagement raised portions 237 engageable with the engagement hole portions 234. This embodiment provides more powerful locking effect than the nineteenth embodiment.

Embodiment 21

Figure 41A:
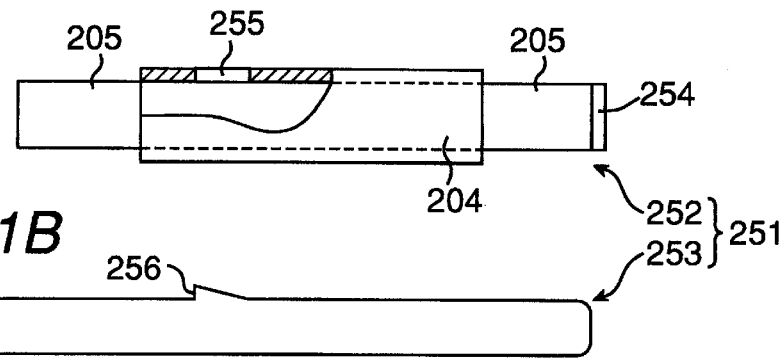
FIGS. 41A and 41B are front views of a holding tube and a spring wire, respectively, in an embodiment 21 of the lock for orthodontic treatment of the invention.
Figure 41B:
Figure 41C:
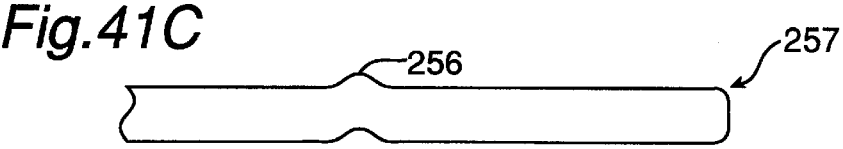
FIG. 41C is a front view of a modified form of the spring wire shown in FIG. 41B.

FIGS. 41A and 41B illustrate a holding tube 252 and a spring wire 253, respectively, of a lock 251 according to a twenty-first embodiment of the invention. In this embodiment, a holding tube 252 includes a bent edge 254, as a first engaging portion, formed by bending perpendicularly to the axis the forward end of a wing portion 205 extending axially from one end of the tubular portion 204 of the holding tube 252, and a hole portion 255, as a second engaging portion, provided in an upper wall adjacent other end of the tubular portion 204. The spring wire 253 is formed thereon with a projection 256 which is engageable with a hole portion 255 of the tubular portion 204 when the tip of the wire is engaged by a bent edge 254 of the tubular portion 204. The projection 256 of the spring wire 266 shown in FIG. 41B may be formed by bending as shown in FIG. 41C with respect to the spring wire 267.

Embodiment 22

Figure 42A:
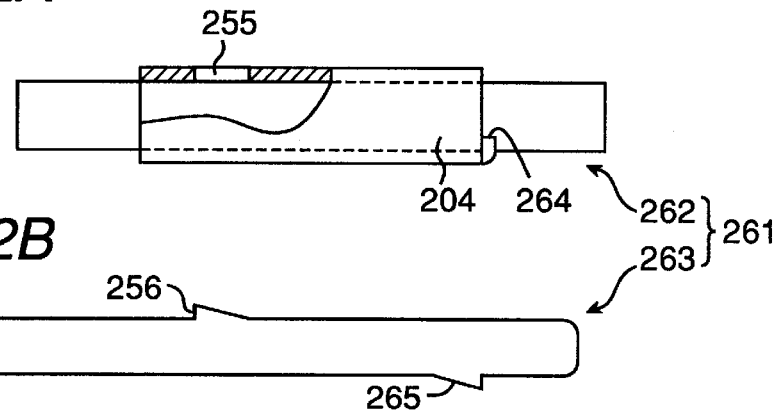
FIGS. 42A and 42B are front views of a holding tube and a spring wire, respectively, in an embodiment 22 of the lock for orthodontic treatment of the invention.
Figure 42B:
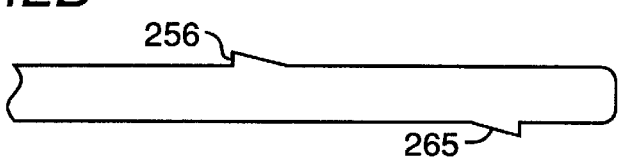
Figure 42C:
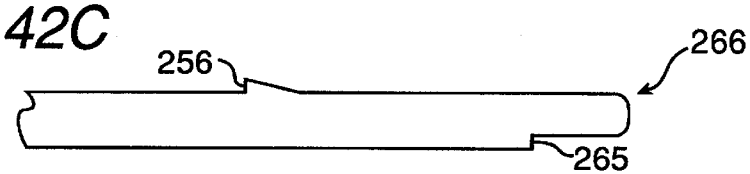
FIGS. 42C and 42D are front views of modified forms of the spring wire shown in FIG. 42B.
Figure 42D:
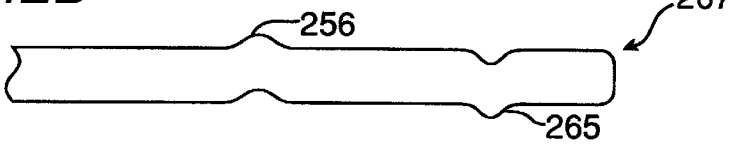

FIGS. 42A and 42B illustrate a holding tube 262 and a spring wire 263, respectively, of a lock 261 according to a twenty-second embodiment of the invention. In this embodiment, the holding tube 262 includes a pawl portion 264 projecting inwardly from a bottom wall edge at one end of the tubular portion 204, and a hole portion 255 formed adjacent an upper wall edge at other end of the tubular portion 204. The spring wire 263 has a projection 265 formed on the underside of one end portion thereof which is engageable with the pawl portion 264 of the holding tube 262, and a projection 256 formed on the upper side of the one end portion which is engageable with the hole portion 255 of the holding tube 262. The projection 265 of the spring wire 263 may be formed in a stepped fashion as in the case of spring wire 266 shown in FIG. 42C, or may be formed by bending as in the case of spring wire 267 shown in FIG. 42D.

Embodiment 23

Figure 43A:
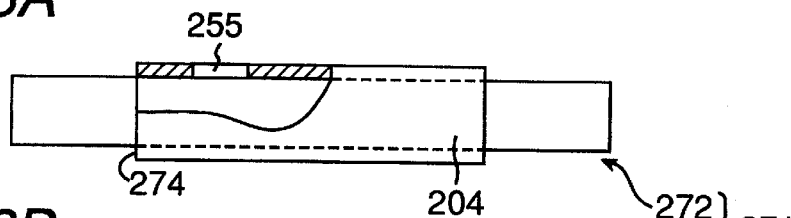
FIGS. 43A and 43B are front views of a holding tube and a spring wire, respectively, in an embodiment 23 of the lock for orthodontic treatment of the invention.
Figure 43B:
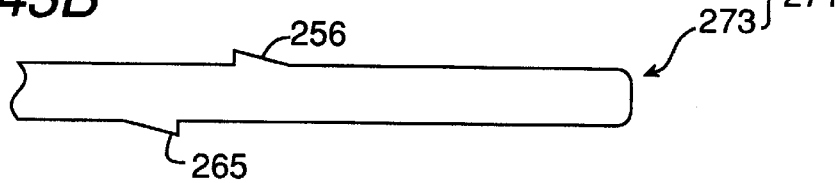
Figure 43C:
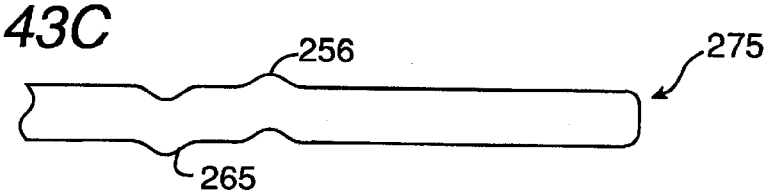
FIG. 43C is a front view of a modified form of the spring wire shown in FIG. 43B.

FIGS. 43A and 43B illustrate a holding tube 272 and a spring wire 273, respectively, of a lock 271 according to a twenty-third embodiment of the invention. In this embodiment, an end edge 274 of the bottom wall at the inlet side of tubular portion 204 of the holding tube 272 takes the part of a first engagement portion, and a hole portion 255 formed on the upper wall adjacent the inlet side of the tubular portion takes the part of a second engagement portion. At one end of the spring wire 273 there are formed a projection 265 engageable with the end edge 274 of the tubular portion 204, and a projection 256 engageable with the hole portion 255 of the tubular portion 204. The projections 256, 265 of the spring wire 273 may be fabricated by bending as in the case of spring wire 275 shown in FIG. 43C.

Embodiment 24

Figure 44A:
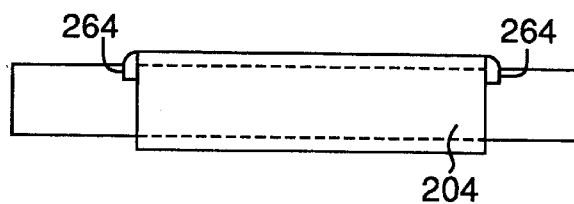
FIGS. 44A and 44B are front views of a holding tube and a spring wire, respectively, in an embodiment 24 of the lock for orthodontic treatment of the invention.
Figure 44B:
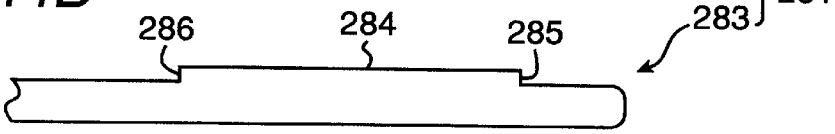

FIGS. 44A and 44B illustrate a holding tube 282 and a spring wire 283, respectively, of a lock 281 according to a twenty-fourth embodiment of the invention. In this embodiment, pawl portions 264, 264 projecting inwardly from upper wall end edges at opposite ends of the tubular portion 204 of the holding tube 282 take the part of a first engagement portion and a second engagement portion. At an end of the spring wire 283 there is formed an engagement raised portion 284 which is slightly shorter than the length of the tubular portion 204. Both ends of the engagement raised portion 284 serve as end edges 285, 286 engageable with the pawl portions 264, 264 of the tubular portion 204.

Embodiment 25

Figure 45A:
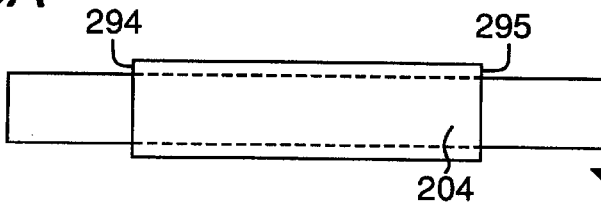
FIGS. 45A and 45B are front views of a holding tube and a spring wire, respectively, in an embodiment 25 of the lock for orthodontic treatment of the invention.
Figure 45B:
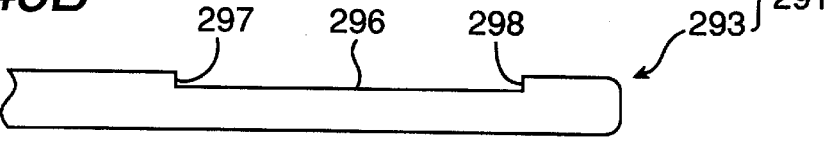

FIGS. 45A and 45B illustrate a holding tube 292 and a spring wire 293, respectively, of a lock 291 according to a twenty-fifth embodiment of the invention. In this embodiment, opposite end edges of upper wall of the tubular portion 204 of the holding tube 292 act as first and second engagement portions respectively. At one end of the spring wire 293 there is formed an engagement recess portion 296 which is slightly longer than the length of the tubular portion 204. Opposite end edges of the engagement recess portion 296 act as end edges 297, 298 engageable with opposite end edges 294, 295 of the tubular portion 204.

With respect to the foregoing embodiments, tubular portion 14, 204 is shown as having an angular sectional configuration, but is not limited to such a configuration. For example, where the spring wire is circular in section, a sectional configuration such that two circles arranged slightly spaced apart are interconnected by a common tangent (an oblong configuration) may be employed to provide a tubular portion having such a sectional configuration. In that case, a wing portion may be formed along one side of the tangent. Where the tubular portion 14, 204 is rectangular in section, the spring wire can be made rectangular in section.

Embodiment 26

In the foregoing 1st through 25th embodiments, a cylindrical holding tube is used as a holding member. However, as will be described hereinafter, a holding member of H shape or channel shape in section may be used.

Figure 46:
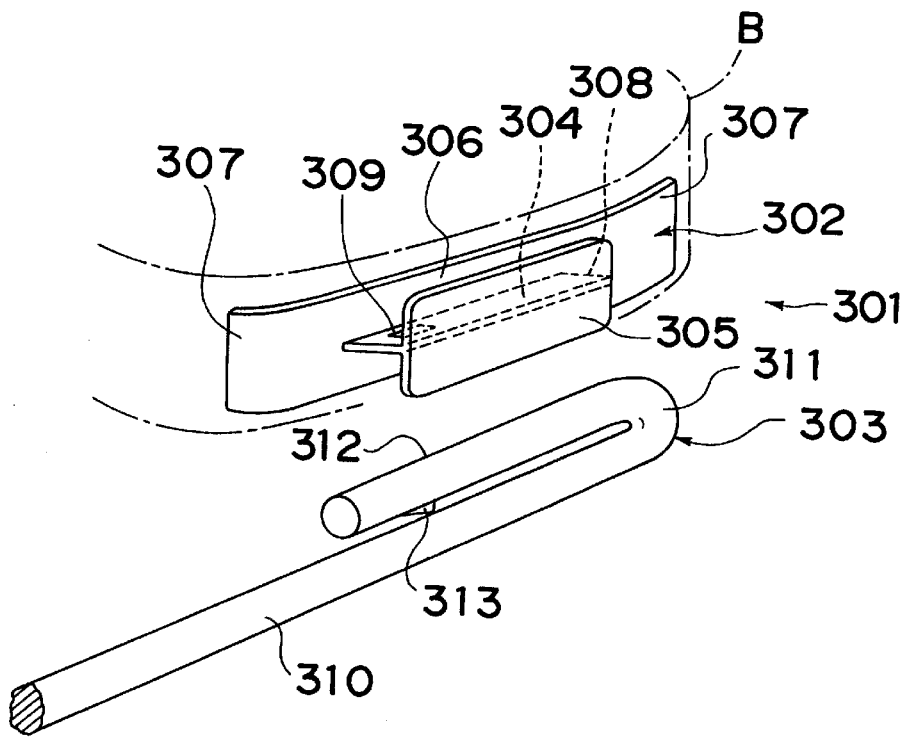
FIG. 46 is a perspective view of an embodiment 26 of the lock for orthodontic treatment of the invention in disengaged condition.
Figure 47:
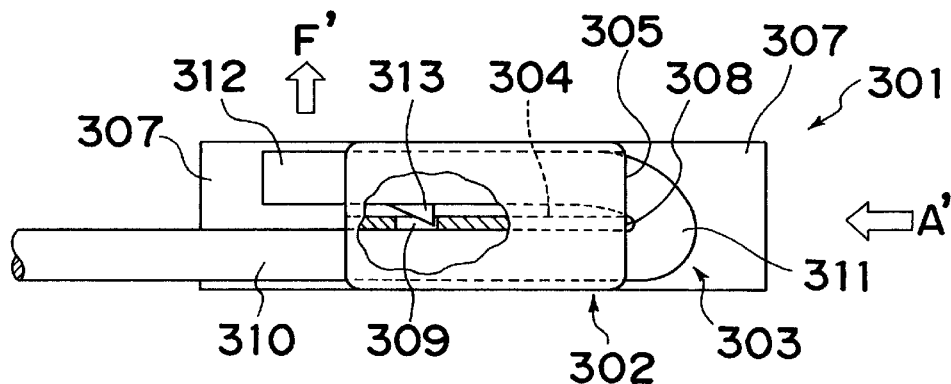
FIG. 47 is a front view of the lock shown in FIG. 46 in engaged condition.

FIGS. 46 and 47 illustrate a lock 301 according to a twenty-sixth embodiment of the invention. In this embodiment, the holder member 302 includes a horizontal web portion 304, and flange portions 305, 306 extending vertically, both upward and downward, from opposite side edges of the web portion 304, and has a sectional configuration of H shape. Corners of the front side flange portion are chamfered round so as not to damage oral mucous membrane. Both ends of the back-side flange portion 306 extend laterally, rightward and leftward, to form wing portions 307. One end edge 308 of the web portion 304 serves as a first engagement portion, and an hole portion 309 formed adjacent the other end of the web portion 304 serves as a second engagement portion.

The spring wire 303, in the same manner as in the first embodiment, is bent via a curved portion at a position adjacent the wire body 310 to define a spring hook portion 312. The spring hook portion 312 is formed with a projection 313 projecting toward the wire body 310. The spacing between the tip of the projection 313 of the spring hook portion 312 and the wire body 310 is set smaller than the thickness of the web portion 304 of the holding member 302. The spacing between the projection 313 of the spring hook portion 312 and the inner surface of the curved portion 311 is set slightly longer than the length of the web portion 304 of the holding member 302.

To mount the spring wire 303 to the holding member 302, the wire body 310 is put to the underside (or upper side) of the web portion 394 and is drawn along the web portion 304 in the direction of arrow A'. As a result, the web portion 304 advances into the space between the spring hook portion 312 and the wire body 310, and the projection 313 of the spring hook portion 312 is pressed by the web portion 304, whereby the distance between the spring hook portion 312 and the wire body 310 is widened. As the spring wire 303 is further drawn, the interior surface of the curved portion 311 abuts one end edge 308 of the web portion 304, and the projection 313 of the spring hook portion 312 comes into engagement with the hole portion 309 of the web portion 394, thereby the spring wire is locked. To remove the spring wire 303, an outer end of the spring hook portion 312 is lifted in the direction of arrow F'. Thereby, the projection 313 of the spring hook portion 312 is disengaged from the hole portion 309 of the web portion 304. Thus, by pushing the spring wire 303 in a direction opposite to the direction of arrow A', the spring wire 303 can be removed from the holding member 302.

Figure 48:
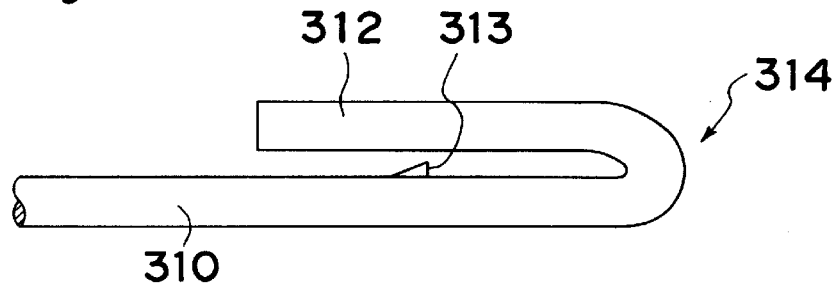
FIG. 48 is a front view of a modified form of the spring wire of the lock shown in FIG. 46.

The projection 313 of the spring wire 303 may be formed on the wirebody 310 so as to project toward the spring hook portion 312 as in a spring wire 314 shown in FIG. 48.

Embodiment 27

Figure 49A:
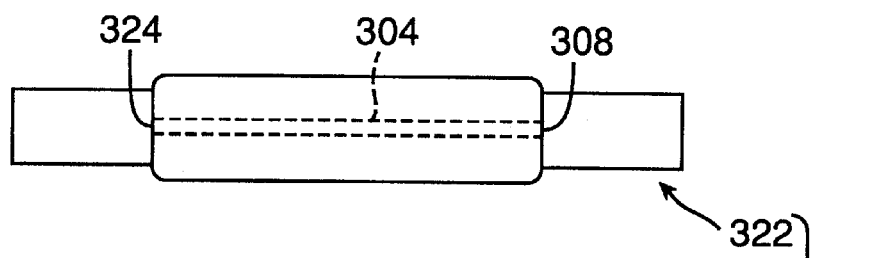
FIGS. 49A and 49B are front views of a holding tube and a spring wire, respectively, in an embodiment 27 of the lock for orthodontic treatment of the invention.
Figure 49B:
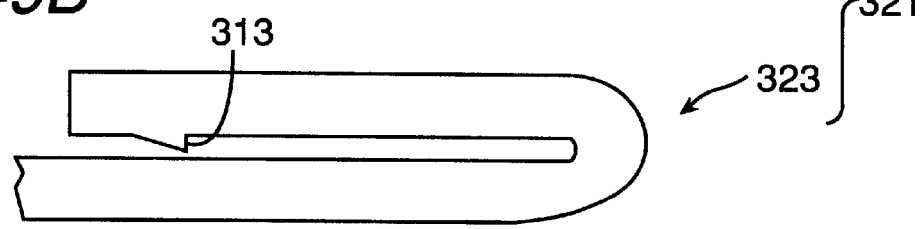

FIGS. 49A and 49B illustrate a holding member 322 and a spring wire 323, respectively, of a lock 321 according to a twenty-seventh embodiment of the invention. In this embodiment, the opening 309 of the twenty-sixth embodiment shown in FIGS. 46 and 47 are not provided, and opposite end edges 308, 324 of the web portion 304 are used respectively as a first engaging portion and a second engaging portion. The locking function of these elements is same as that of the twenty-sixth embodiment.

Embodiment 28

Figure 50A:
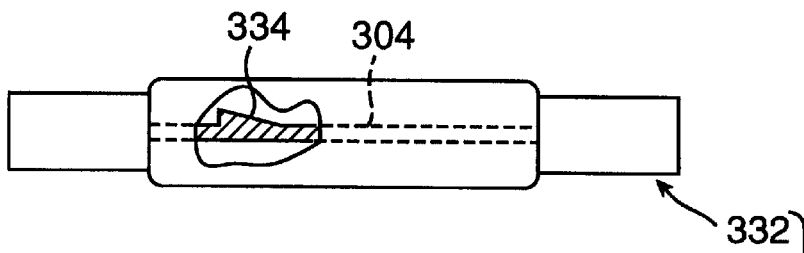
FIGS. 50A and 50B are front views of a holding tube and a spring wire, respectively, in an embodiment 28 of the lock for orthodontic treatment of the invention.
Figure 50B:
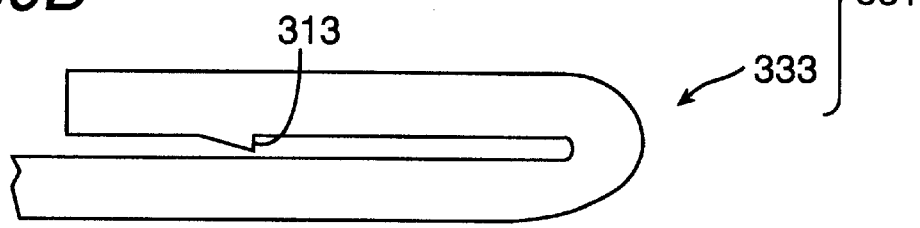

FIGS. 50A and 50B illustrate a holding member 332 and a spring wire 333, respectively, of a lock 331 according to a twenty-eighth embodiment of the invention. In this embodiment, a projection 334 engageable with the projection 313 of the spring wire 323 is provided in place of the opening 309 in the twenty-sixth embodiment shown in FIGS. 46 and 47. The locking function of the projection is same as that in the twenty-sixth embodiment.

Embodiment 29

Figure 51A:
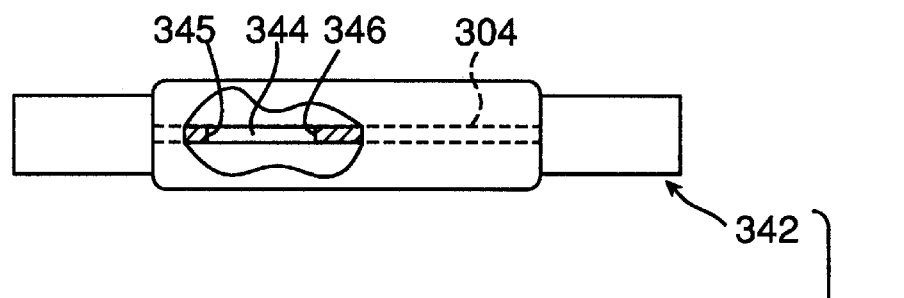
FIGS. 51A and 51B are front views of a holding tube and a spring wire, respectively, in an embodiment 29 of the lock for orthodontic treatment of the invention.
Figure 51B:
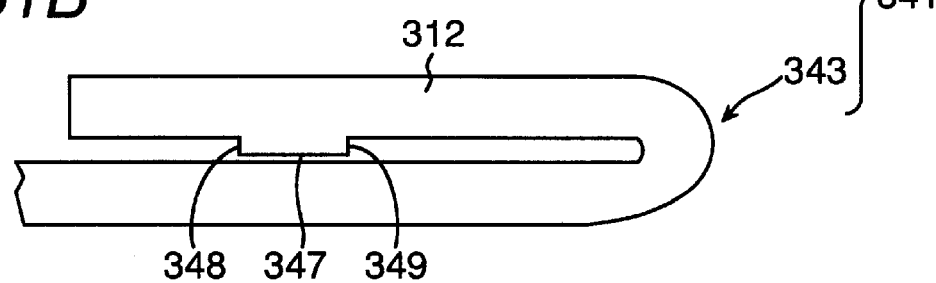

FIGS. 51A and 51B illustrate a holding member 342 and a spring wire 343, respectively, of a lock 341 according to a twenty-ninth embodiment of the invention. In this embodiment, the web portion 304 of the holding member 342 has an engagement hole portion 344 formed therein, both end edges 345, 346 of which serve as a first engagement portion and a second engagement portion respectively. The spring hook portion 312 of the spring wire 343 is formed with an engagement raised portion 347 for engagement with the engagement hole portion 344, opposite ends 348, 349 of which serve as end edges.

Embodiment 30

Figure 52A:
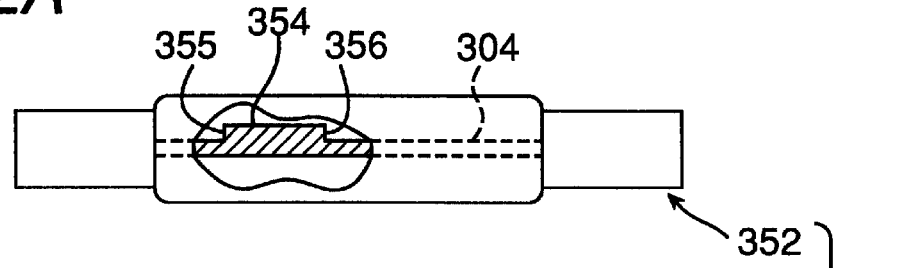
FIGS. 52A and 52B are front views of a holding tube and a spring wire, respectively, in an embodiment 30 of the lock for orthodontic treatment of the invention.
Figure 52B:
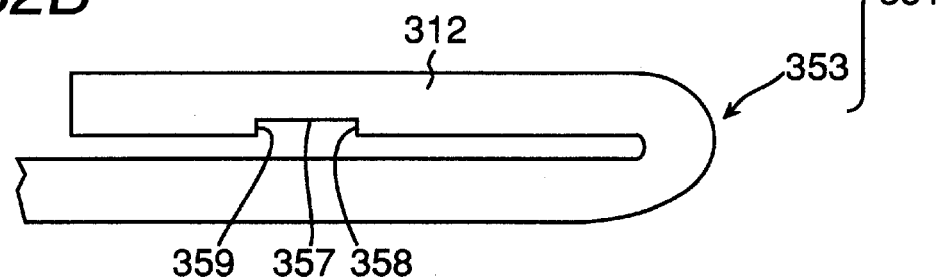
Figure 53:
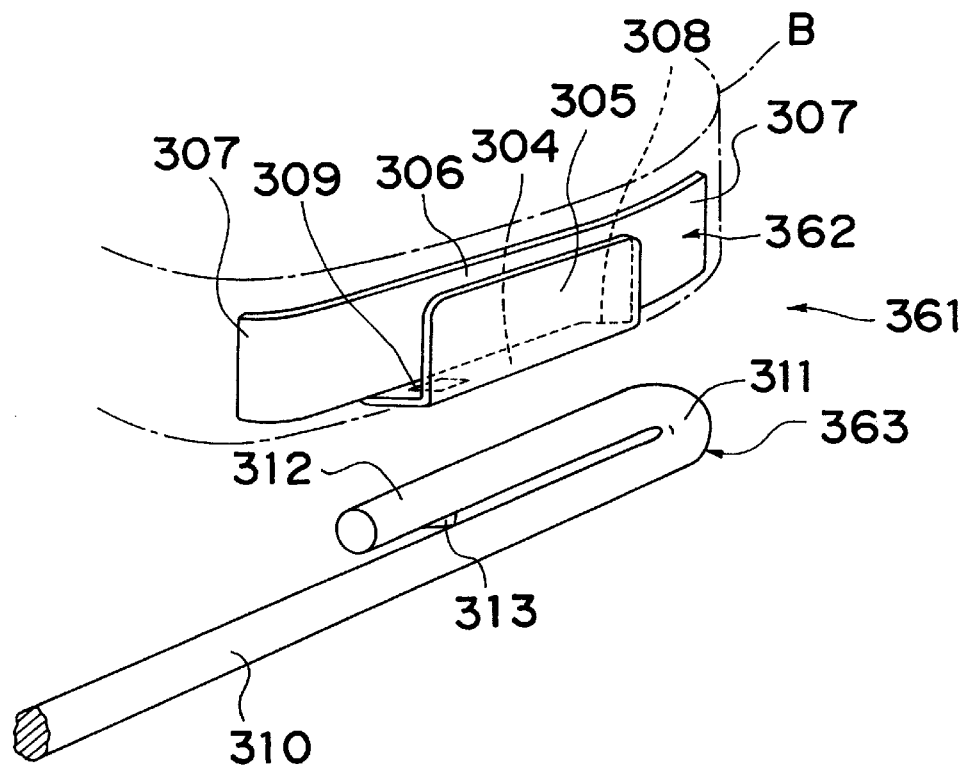
FIG. 53 is a perspective view of an embodiment 31 of the lock for orthodontic treatment of the invention in disengaged condition.
Figure 54:
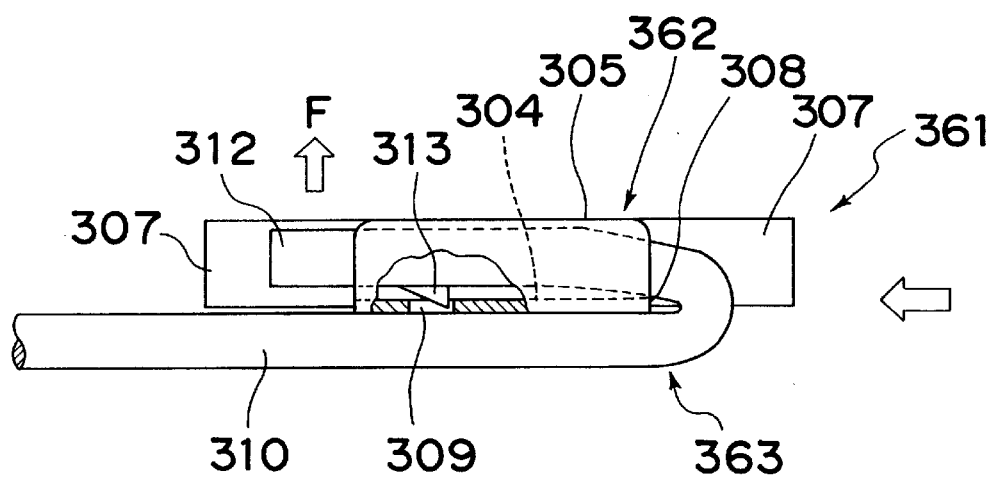
FIG. 54 is a front view of the lock shown in FIG. 53 in engaged condition.
Figure 55:
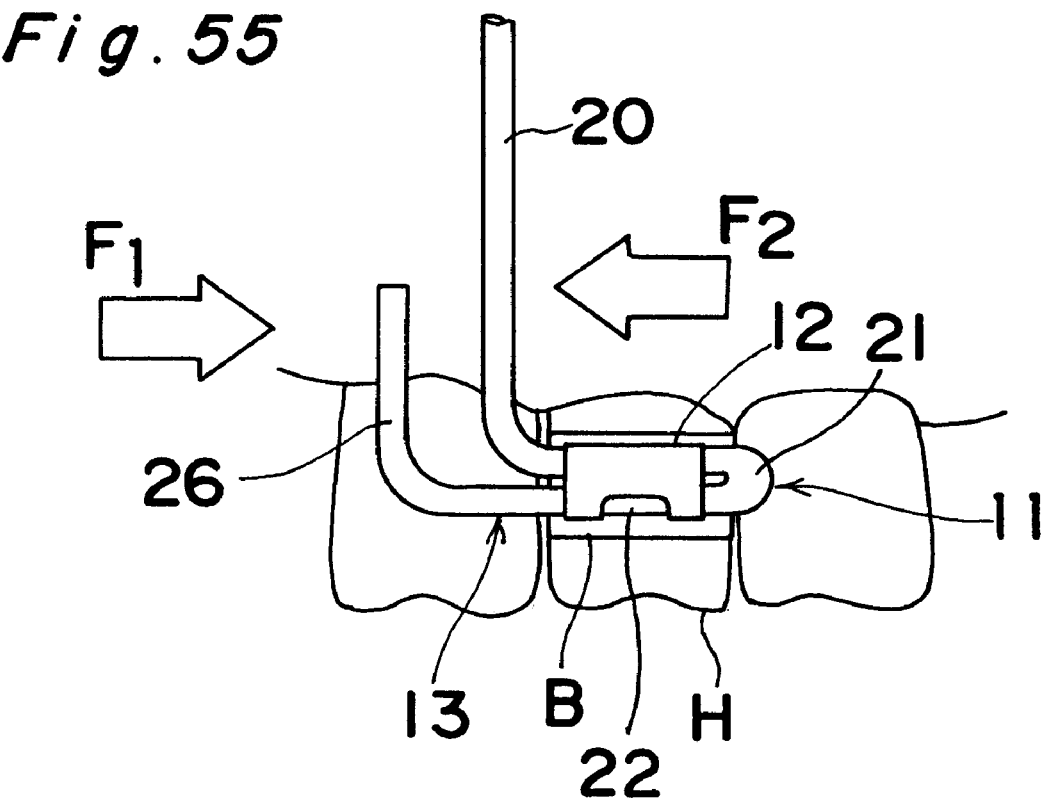
FIG. 55 is a view of the lock for orthodontic treatment of the invention illustrating a use condition.
Figure 56:
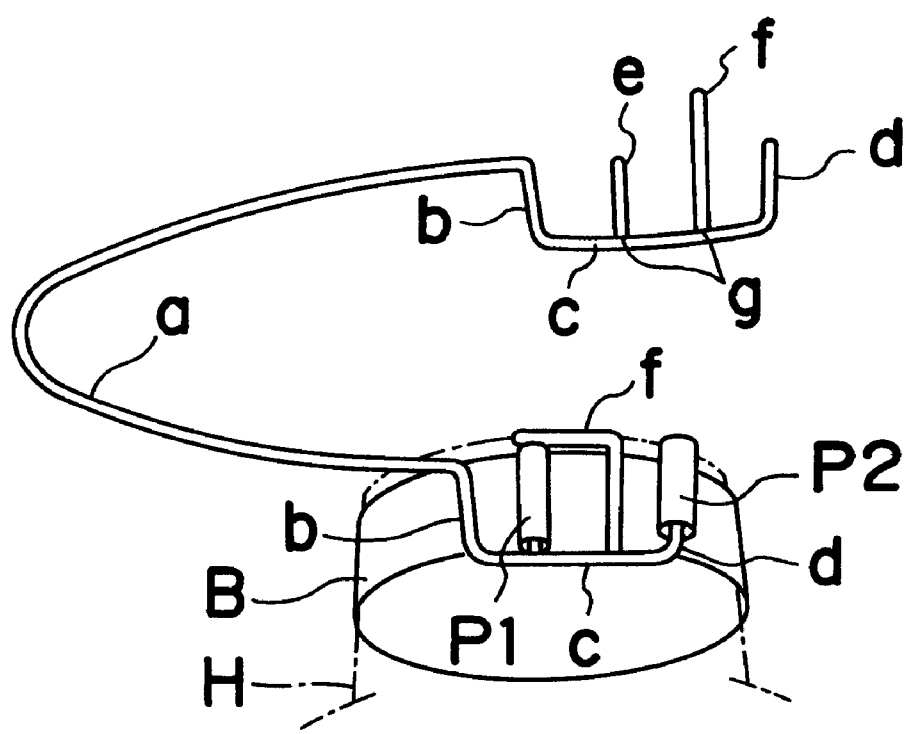
FIG. 56 is a explanatory view of a prior art device.

FIGS. 52A and 52B illustrate a holding member 352 and a spring wire 353, respectively, of a lock 351 according to a thirtieth embodiment of the invention. In this embodiment, an engagement raised portion 354 is provided in place of the engagement hole portion 344 of the web portion 304 of the holding member 342 in the twenty-ninth embodiment shown in FIGS. 51A and 51B. Opposite ends 355, 356 of the engagement raised portion 354 serve as a first engagement portion and a second engagement portion respectively. The spring hook portion 312 of the spring wire 353 is provided with an engagement recess portion 357 for engagement with the engagement raised portion 354. Opposite ends 358, 359 of the engagement recess portion 357 serve as end edges.

Embodiment 31

Figure 16:
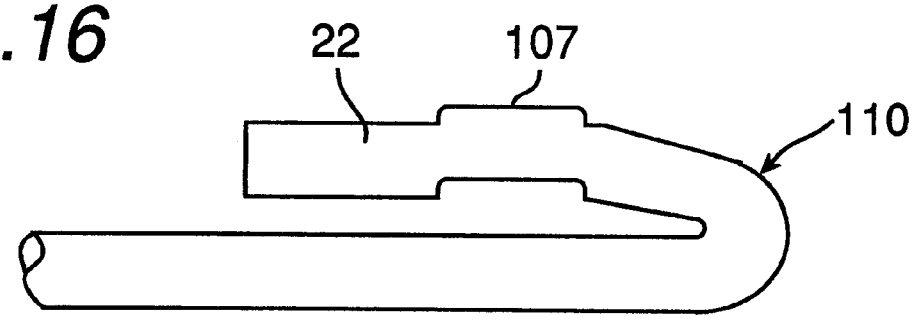
FIG. 16 is a front view of the lock shown in FIG. 15 in engaged condition.

FIGS. 15 and 16 shows a lock 361 according to a thirty-first embodiment of the invention. This embodiment is identical with the twenty-sixth embodiment shown in FIGS. 46 and 47, except that the holding member 362 includes a horizontal web portion 304, and flange portions 305, 306 extending vertically upward from two opposite ends of the web portion 304, and that the holding member 362 has a sectional configuration of channel shape. The locking effect of the embodiment is identical with the latter mentioned embodiment. Therefore, description is omitted. Embodiments and modifications shown in FIGS. 14A, 14B and 48 through 51B are equally applicable to this thirty-first embodiment.

Application Example

Figure 17:
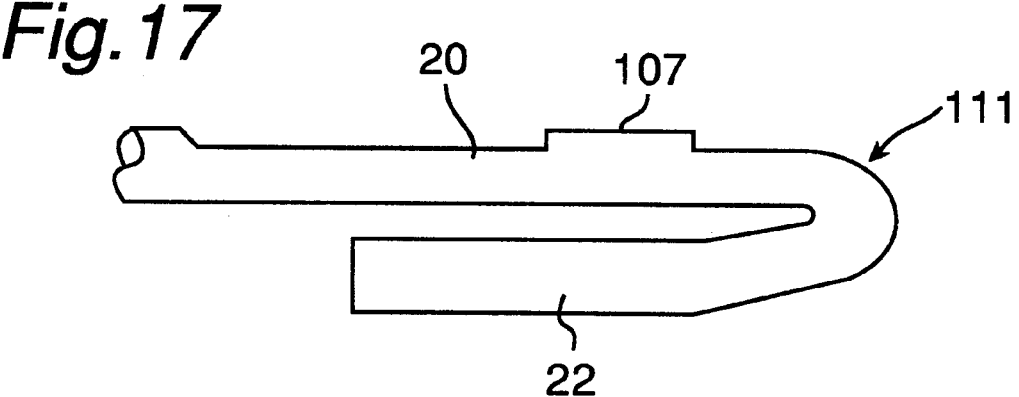
FIG. 17 is a view of the lock for orthodontic treatment of the invention illustrating a use condition.

FIG. 17 shows the lock 11 for orthodontic treatment of the present invention as actually applied to a molar tooth H of upper jaw of a patient. The ends of the wire body 20 of the spring wire 13 are bent about 90°, with the spring hook portion 22 formed via the curved portion 21. The outer end portion 26 of the spring hook portion 22 is bent 90° so that it extends in parallel relation to the wire body 20. The holding tube 12 is securely fixed to the inner side of the band B mounted to the molar tooth H of the patient. The spring wire 13 and the holding tube 12 are equipped with the lock of the present invention as described with respect to the foregoing embodiments. To remove the spring wire 13 after its has been mounted to the holding tube 12, the outer end 26 of the spring hook portion 22 is depressed in the direction of arrow F1 to disengage the lock. By drawing the wire body 20 in the direction of arrow F2, the wire can be removed from the holding tube 12.

What is claimed is:

1. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is formed with an engagement surface portion such that one end edge of the engagement surface portion acts as the first engagement portion and other end edge acts as the second engagement portion, and the spring hook portion or a wire body which is opposed to the spring hook portion is formed with a cutout surface portion at a position opposite to the engagement surface portion such that one end of the cutout surface portion acts as the first locking portion and other end acts as the second locking portion.

2. A lock for orthodontic treatment as set forth in claim 1, wherein a window is provided on the upper side or lower side of the holding tube such that at least one side of the window acts as the engagement surface portion.

3. A lock for orthodontic treatment as set forth in claim 1, wherein the entire upper or lower side of the holding tube is made to act as the engagement surface portion.

4. A lock for orthodontic treatment as set forth in claim 1, wherein the holding tube is formed with a pair of engagement surface portions with a space portion provided therebetween, and wherein the spring hook portion or a wire body which is opposed to the spring hook portion is formed with a pair of cutout surface portions spaced at a distance corresponding to the space portion.

5. A lock for orthodontic treatment as set forth in claim 1, wherein the holding tube is provided with a window such that opposite sides of the window act as a pair of engagement surface portions, and wherein the spring hook portion is formed with a pair of cutout surface portions corresponding to the engagement surface portions.

6. A lock for orthodontic treatment as set forth in claim 5, wherein the window is provided at both upper and lower sides of the holding tube.

7. A lock for orthodontic treatment as set forth in claim 1, wherein the surface engagement portion is formed with projections and depressions arranged in succession, and the cutout surface portion is formed with depressions and projections arranged in succession for engagement with the projections and depressions.

8. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is formed with one or more engagement surface portions projecting inwardly of the holding tube such that one end edge of the engagement surface portion acts as the first engagement portion and other end edge acts as the second engagement portion, and the spring hook portion or a wire body which is opposed to the spring hook portion is formed with one or more cutout surface portion at positions opposite to the engagement surface portions such that one end of the cutout surface portion acts as the first locking portion and other end of the cutout surface portion acts as the second locking portion.

9. A lock for orthondontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is removed axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is formed with a plurality of engagement hold portions such that one edge of the engagement hole portion acts as the first engagement portion and other edge acts as the second engagement portion, and the spring hook portion or a wire body which is opposed to the spring hook portion is formed with a plurality of engagement raised portions engageable with the one or more engagement hole portions such that one end of the engagement raised portion acts as the first locking portion and other end acts as the second locking portion.

10. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a bent edge extending axially from one end of the holding tube and having a portion bent perpendicularly to the axial direction, and with a pawl projection extending axially from the other end of the holding tube and having a portion projecting perpendicularly to the axial direction, such that the bent edge acts as the first engagement portion and the pawl projection acts as the second engagement portion, and an outer curved portion of the spring hook portion acts as the first locking portion, and a projection formed on the spring hook portion or a wire body which is opposed to the spring hook portion acts as the second locking portion.

11. A lock for orthondontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a bent edge extending axially from one end of the holding tube and having a portion bent perpendicularly to the axial direction, and with a hole portion located adjacent the other end of the holding tube, such that the bent edge acts as the first engagement portion and the hole portion acts as the second engagement portion, and an outer curved portion of the spring hook portion acts as the first locking portion, tip end corner of a bent portion formed by bending outwardly the end of the spring hook portion acts as the second locking portion.

12. A lock for orthondontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire is a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the fist locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a bent edge extending axially from one end of the holding tube and having a portion bent perpendicularly to the axial direction, and with a hole portion located adjacent the other end of the holding tube, such that the bent edge acts as the first engagement portion and the hole portion acts as the second engagement portion, and an outer curved portion of the spring hook portion acts as the first locking portion, a projection formed on the spring hook portion or a wire body which is opposed to the spring hook portion acts as the second locking portion.

13. A lock for orthondontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a pawl portion projecting inwardly from one end edge of the holding tube, and a pawl projection extending axially from the other end and having a portion projecting perpendicularly to the axial direction, such that the pawl portion acts as the first engagement portion and the pawl projection acts as the second engagement portion, and a projection formed on one of the spring hook portion or a wire body which is opposed to the spring hook portion acts as the first locking portion, and a projection formed on the other of the spring hook portion or the wire body acts as the second locking portion.

14. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a pawl portion projecting inwardly from one end edge of the holding tube, and a hold portion located adjacent the other end of the holding tube, such that the pawl portion acts as the first engagement portion and the hole portion acts as the second engagement portion, and a projection formed on one of the spring hook portion or a wire body which is opposed to the spring hook portion acts as the first locking portion, and a projection formed on the other of the spring hook portion or the wire body acts as the second locking portion.

15. A lock for orthondontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a pawl portion projecting inwardly from one end edge of the holding tube, and a pawl projection extending axially from the other end and having a portion projecting perpendicularly to the axial direction, such that the pawl portion acts as the first engagement portion, and the pawl projection acts as the second engagement portion, and one of two projections formed on any one of the spring hook portion or a wire body which is opposed to the spring hook portion acts as the first locking portion, the other acts as the second locking portion.

16. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein the holding tube is provided with a pawl portion projecting inwardly from one end edge of the holding tube, and a hole portion located adjacent the other end of the holding tube, such that the pawl portion acts as the first engagement portion and the hole portion acts as the second engagement portion, and one of two projections formed on any one of the spring hook portion or a wire body which is opposed to the spring hook portion acts as the first locking portion, the other acts as the second locking portion.

17. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking position for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring wire is bent at a position adjacent to the end thereof to form a spring hook portion having elasticity, and wherein an inlet side end edge of the holding tube acts as the first engagement portion and a pawl projection extending axially from the inlet side end edge and having a portion projecting perpendicularly to the axial direction acts as the second engagement portion, and a projection formed on one of the spring hook portion or a wire body which is opposed to the spring hook portion acts as the first locking portion, and a projection formed on the other of the spring hook portion or the wire body acts as the second locking portion.

18. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member wherein the holding member is a cylindrical holding tube adapted to receive the spring wire, wherein the holding tube has elastic properties because of the presence of a slit formed longitudinally of the holding tube.

19. A lock for orthodontic treatment as set forth in claim 18, wherein the holding tube is formed with one or more engagement surface portions projecting inwardly of the holding tube such that one end edge of the engagement surface portion acts as the first engagement portion and other end edge acts as the second engagement portion, and the spring wire is formed with one or more cutout surface portions at positions opposite to the engagement surface portions such that one end of the cutout surface portion acts as the first locking portion and other end acts as the second locking portion.

20. A lock for orthodontic treatment as set forth in claim 11, wherein the holding tube is formed with one or more engagement hole portions such that one edge of the engagement hole portion acts as the first engagement portion and other edge acts as the second engagement portion, and the spring wire is formed with one or more engagement raised portions for engagement with the engagement hole portion or portions such that one end of the engagement raised portion acts as the first locking portion and other end acts as the second locking portion.

21. A lock for orthodontic treatment as set forth in claim 18, wherein the holding tube is provided with a bent edge extending axially from one end of the holding tube and having a portion bent perpendicularly to the axial direction, and with a hole portion located adjacent the other end of the holding tube, such that the bent edge acts as the first engagement portion and the hole portion acts as the second engagement portion, and a distal end of the spring wire acts as the first locking portion and a projection formed on the spring wire acts as the second locking portion.

22. A lock for orthodontic treatment as set forth in claim 18, wherein the holding tube is provided with a pawl portion projecting inwardly from one end edge of the holding tube, and a hole portion located adjacent the other end of the holding tube, such that the pawl portion acts as the first engagement portion and the hole portion acts as the second engagement portion, and one of two projections formed on the spring wire acts as the first locking portion, the other acts as the second locking portion.

23. A lock for orthodontic treatment as set forth in claim 18, wherein an inlet side end edge of the holding tube acts as the first engagement portion and a pawl portion projecting inwardly from the inlet side end edge acts as the second engagement portion, and one of two projections formed on the spring wire acts as the first locking portion, the other acts as the second locking portion.

24. A lock for orthodontic treatment as set forth in claim 18, wherein an inlet side end edge of the holding tube acts as the first engagement portion and a hole portion located adjacent the inlet side end edge of the holding tube acts as the second engagement portion, and one of two projections formed on the spring wire acts as the first locking portion, the other acts as the second locking portion.

25. A lock for orthodontic treatment as set forth in claim 18, wherein the holding tube is provided with pawl portions projecting inwardly from opposite end edges of the holding tube, such that one of the pawl portions acts as the first engagement portion the other acts as the second engagement portion, and the spring wire is formed with an engagement raised portion to be held between the pawl portions, such that one end of the engagement raised portion acts as the first locking portion and the other end acts as the second locking portion.

26. A lock for orthodontic treatment as set forth in claim 18, wherein an inlet side end edge of the holding tube acts as the first engagement portion and an outlet side end edge of the holding tube acts as the second engagement portion, and the spring wire is formed with an engagement depressed portion to be held between the two edges, such that one end of the engagement depressed portion acts as the first locking portion, the other end acts as the second locking portion.

27. A lock for orthodontic treatment as set forth in claim 18, wherein the spring hook portion is formed, at a position spaced from the distal end of the spring wire by at least the length of the holding tube, with a flat crushed portion such that the flat crushed portion engages with an inlet side edge of the holding tube to prevent the spring hook portion from projecting through a tubular portion.

28. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member includes a web portion and flange portions extending from opposite ends of the web portion and has a sectional configuration of H shape or channel shape, the spring wire is bent at a position adjacent to the end thereof to form a spring hook portion having elasticity, and the web portion of the holding member is positioned in a gap between the spring hook portion and the wire body whereby the spring wire is held in position.

29. A lock for orthodontic treatment as set forth in claim 28, wherein one end of the web portion of the holding member acts as the first engagement portion, and a hole portion provided adjacent the other end of the web portion acts as the second engagement portion, and inner surface of a curved portion of the spring wire acts as the first locking portion, a projection formed on the spring hook portion or the wire body which is opposed to the spring hook portion acts as the second locking portion.

30. A lock for orthodontic treatment as set forth in claim 28, wherein one end of the web portion of the holding member acts as the first engagement portion, and the other end acts as the second engagement portion, and inner surface of a curved portion of the spring wire acts as the first locking portion, a projection formed on the spring hook portion or the wire body which is opposed to the spring hook portion acts as the second locking portion.

31. A lock for orthodontic treatment as set forth in claim 28, wherein one end of the web portion of the holding member acts as the first engagement portion, and a projection provided adjacent the other end acts as the second engagement portion, and inner surface of a curved portion of the spring wire acts as the first locking portion, a projection formed on the spring hook portion or the wire body which is opposed to the spring hook portion acts as the second locking portion.

32. A lock for orthodontic treatment as set forth in claim 28, wherein the web portion of the holding tube is formed with one or more engagement hole portions such that one end edge of the engagement hole portion acts as the first engagement portion and other end edge acts as the second engagement portion, and the spring wire is formed, on the spring hook portion or the wire body which is opposed to the spring hook portion, with one or more engagement raised portions for engagement with the engagement hole portion or portions, such that one end of the engagement raised portion acts as the first locking portion and other end acts as the second locking portion.

33. A lock for orthodontic treatment as set forth in claim 28, wherein the web portion of the holding tube is formed with one or more engagement raised portions such that one end edge of the engagement raised portion acts as the first engagement portion and other end edge acts as the second engagement portion, and the spring wire is formed, on the spring hook portion or the wire body which is opposed to the spring hook portion, with one or more engagement recess portions for engagement with the engagement raised portion or portions, such that one end of the engagement recess portion acts as the first locking portion and other end acts as the second locking portion.

34. A lock for orthodontic treatment, comprising a holding member fixed to a molar band, and a spring wire having an end removably held by the holding member, the holding member being configured such that the end of the spring wire is held on the holding member by being moved axially along the holding member, one of the holding member and the spring wire having elasticity in a direction perpendicular to its axis, the holding member including a first engagement portion for preventing the movement of the end of the spring wire in a mounting direction, and a second engagement portion for preventing the movement of the end of the spring wire in a removing direction, and the spring wire including a first locking portion for engaging with the first engagement portion of the holding member, and a second locking portion for engaging with the second engagement portion of the holding member, whereby, when the end of the spring wire is moved axially along the holding member and held on the holding member, the first locking portion of the spring wire engages with the first engagement portion of the holding member and the second locking portion of the spring wire engages with the second engagement portion of the holding member under the elasticity of one of the holding member and the spring wire so that the spring wire is locked by the holding member, wherein the holding member is a cylindrical holding tube adapted to receive the spring wire, wherein the spring hook portion is formed at its end with a flat crushed portion such that the flat crushed portion engages with an inlet side end edge of the holding tube to prevent the spring hook portion from projecting through a tubular portion.

\* \* \* \* \*